(12) United States Patent
Domènech Garcia et al.

(10) Patent No.: US 12,280,033 B2
(45) Date of Patent: *Apr. 22, 2025

(54) PHARMACEUTICAL COMBINATION FOR THE TREATMENT OF A CANCER

(71) Applicant: ABILITY PHARMACEUTICALS S.L., Cerdanyola del Vallès (ES)

(72) Inventors: Carles Domènech Garcia, Cerdanyola del Vallès (ES); José Alberto Alfón Coriat, Cerdanyola del Vallès (ES); Héctor Pérez Montoyo, Cerdanyola del Vallès (ES); Miguel Francisco Segura Ginard, Cerdanyola del Vallès (ES); Jose Miguel Lizcano De Vega, Cerdanyola del Vallès (ES)

(73) Assignee: ABILITY PHARMACEUTICALS S.L., Cerdanyola del Vallès (ES)

( * ) Notice: Subject to any disclaimer, the term of this patent is extended or adjusted under 35 U.S.C. 154(b) by 0 days.

This patent is subject to a terminal disclaimer.

(21) Appl. No.: 18/763,671

(22) Filed: Jul. 3, 2024

(65) Prior Publication Data

US 2024/0350449 A1 Oct. 24, 2024

Related U.S. Application Data

(63) Continuation of application No. 17/581,587, filed on Jan. 21, 2022, now Pat. No. 12,053,449, which is a continuation of application No. 16/614,084, filed as application No. PCT/EP2018/062554 on May 15, 2018, now Pat. No. 11,260,042.

(30) Foreign Application Priority Data

May 16, 2017 (EP) ..................................... 17382282

(51) Int. Cl.
| | |
|---|---|
| A61K 31/201 | (2006.01) |
| A61K 31/28 | (2006.01) |
| A61K 31/282 | (2006.01) |
| A61K 31/335 | (2006.01) |
| A61K 31/337 | (2006.01) |
| A61K 31/517 | (2006.01) |
| A61K 31/555 | (2006.01) |
| A61K 33/243 | (2019.01) |
| A61K 45/06 | (2006.01) |
| A61P 35/00 | (2006.01) |
| A61P 35/04 | (2006.01) |

(52) U.S. Cl.
CPC .......... *A61K 31/282* (2013.01); *A61K 31/201* (2013.01); *A61K 31/337* (2013.01); *A61K 33/243* (2019.01); *A61K 45/06* (2013.01); *A61P 35/04* (2018.01)

(58) Field of Classification Search
CPC .. A61K 31/201; A61K 31/555; A61K 31/517; A61K 31/335; A61K 31/28; A61P 35/00

USPC ...................... 514/560, 184, 262.1, 449, 492
See application file for complete search history.

(56) References Cited

U.S. PATENT DOCUMENTS

| | | |
|---|---|---|
| 8,735,436 B2 | 5/2014 | Hovland et al. |
| 9,050,308 B2 | 6/2015 | Maines et al. |
| 11,260,042 B2* | 3/2022 | Domènech García et al. ............. A61P 35/04 |
| 12,053,449 B2* | 8/2024 | Domènech García et al. ............. A61K 31/203 |
| 2004/0053882 A1 | 3/2004 | Smith et al. |
| 2006/0058311 A1 | 3/2006 | Munzert et al. |
| 2014/0271562 A1 | 9/2014 | Garcia-Rodenas et al. |

FOREIGN PATENT DOCUMENTS

| | | |
|---|---|---|
| EP | 2409963 B1 | 1/2017 |
| RU | 2284818 C2 | 6/2004 |
| WO | WO-2018210830 A1 | 11/2018 |

OTHER PUBLICATIONS

AbilityPharmaceuticalsAnnouncesFDA-Orphan Drug Designationfor ABTLO0812inPancreaticCancer, Dec. 14, 2016, accessedat https//avwow.abillitvpharma.com/on/mainimenu/media-centerpresse-reloase/abihity~pharmaceuticals-announces-fda-arphan-dme-designation-forabtlos12-in-pancreatic-cancer, 5pages (Year: 2016).*

AbilityPharma, "Ability Pharmaceuticals Announces FDA-Orphan Drug Designation for ABTL0812 in Pancreatic Cancer", Dec. 14, 2016, accessed at https://www.abilitypharma.com/en/main-menu/media-center/press-release/ability-pharmaceuticals-announces-fda-orphan-drug-designation-for-abtl0812-in-pancreatic-cancer, 5 pages.

AbilityPharma, "Ability Pharmaceuticals Initiates Phase 2 Combination Trial with ABTL0812 as First Line Therapy in Patients with Endometrial or Squamous Lung Cancer Patients", Nov. 22, 2016, accessed at https://www.abilitypharma.com/en/main-menu/media-center/press-release/ability-pharmaceuticals-initiates-phase-2-combination-trial-with-abtl0812-as-first-line-therapy-in-patients-with-endometrial-or-squamous-lung-cancer-patients, 5 pages.

Alfon, J., et al., "Effect of ABTL0812, a safe dual inhibitor of mTORC1/C2 and dihydrofolate reductase, on gemcitabine and docetaxel cytotoxicity in pancreatic and lung cancer cells," Journal of Clinical 31:15, American Society of Clinical Oncology Journal, United States (2013).

Colas, E., et al., "The first-in-class anti-cancer agent ABTL0812 is effective in preclinical models of human endometrial cancer," Journal of Clinical Oncology 35(15):e17070, American Society for Clinical Cancer Research, United States (2017).

Erazo, T., et al., "The New Antitumor Drug ABTL0812 Inhibits the Akt/mTORCI Axis by Upregulating Tribbles-3 Pseudokinase," Clin Cancer Res. 22(10):2508-2519, American Association for Cancer Research, United States (May 2016).

(Continued)

*Primary Examiner* — Raymond J Henley, III
(74) *Attorney, Agent, or Firm* — Sterne, Kessler, Goldstein & Fox P.L.L.C.

(57) ABSTRACT

A pharmaceutical combination comprising (A): a polyunsaturated fatty acid and (B): a chemotherapeutic agent compound for the simultaneous, separate or sequential use in the treatment of a cancer in a human patient.

20 Claims, 17 Drawing Sheets

(56) References Cited

OTHER PUBLICATIONS

Figure 1:
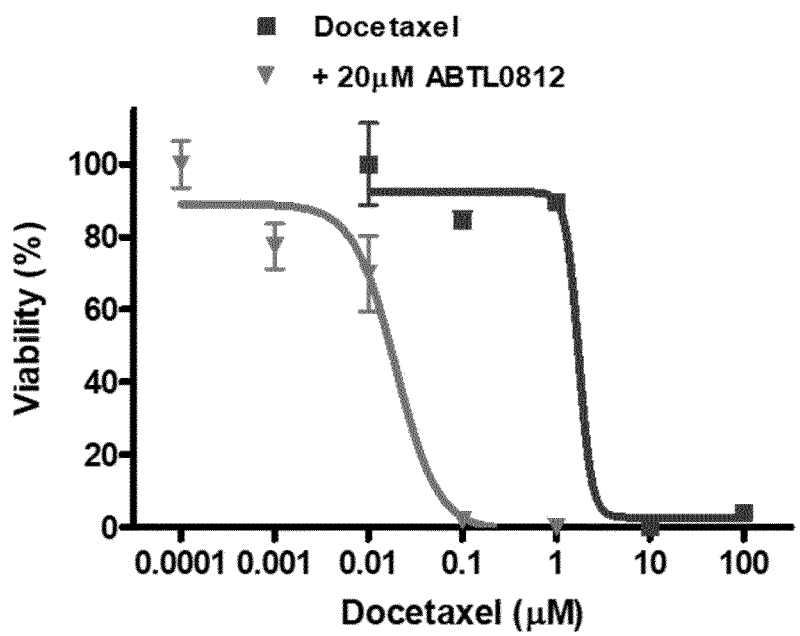
Figure 1:
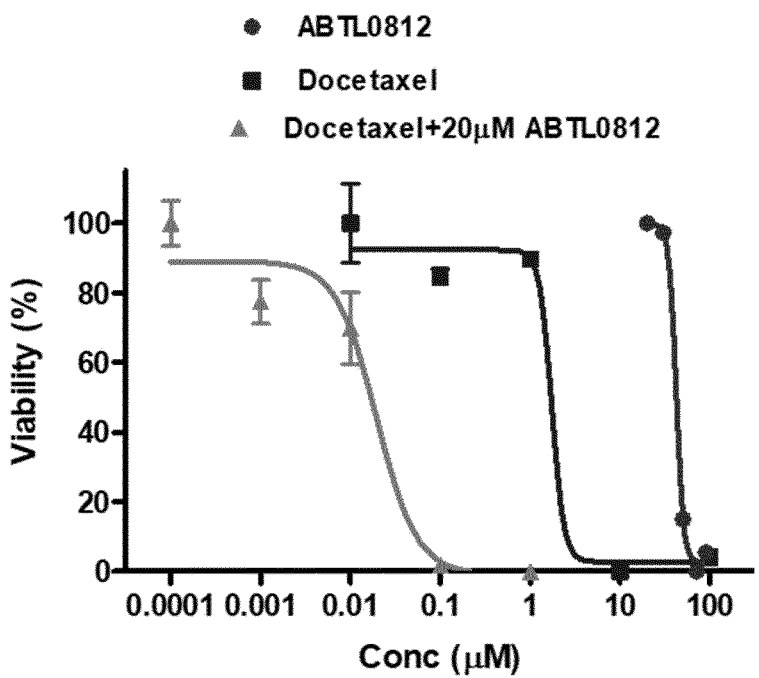

International Search Report and Written Opinion for International Application No. PCT/EP2018/062554, European Patent Office, Netherlands, mailed on Aug. 3, 2018, 10 pages.
Google Patents, English-language Machine Translation of Russian Patent RU-2284818-C2, performed on Mar. 4, 2024, 9 pages.

* cited by examiner

|  | IC50 (µM) |
|---|---|
| ABTL0812 | 33.0 |
| Carboplatin | 112.6 |
| Carboplatin + 4 µM ABTL0812 | 38.0 |

* significantly different Placebo vs ABTL+CBPT-PTX
+ significantly different Placebo vs CBPT-PTX
& significantly different Pacebo vs ABTL
= significantly different ABTL vs ABTL+CBPT-PTX
ç significantly different CBPT-PTX vs ABTL+CBPT-PTX

A

B

PHARMACEUTICAL COMBINATION FOR THE TREATMENT OF A CANCER

CROSS-REFERENCE TO RELATED APPLICATIONS

The present patent application is a continuation of pending U.S. application Ser. No. 17/581,587, filed Jan. 21, 2022, which is a continuation of U.S. application Ser. No. 16/614,084, with 371 (c) date of Nov. 15, 2019, which issued as U.S. Pat. No. 11,260,042, which is the national phase application of International Application No. PCT/US2018/062554, filed May 15, 2018, which claims the priority benefit of European Application No. EP17382282.6, filed on May 16, 2017, all of which are hereby incorporated by reference in their entireties.

FIELD OF THE INVENTION

The present invention relates to a pharmaceutical combination comprising (A): a polyunsaturated fatty acid and (B): a chemotherapeutic agent compound for the simultaneous, separate or sequential use in the treatment of a cancer in a human patient.

STATEMENT REGARDING PRIOR ART DISCLOSURES BY THE INVENTOR OF A JOINT INVENTOR UNDER 37 C.F.R. 1.77(b)(6)

At the filing date of the present application—the webpage of the present applicant (AbilityPharma-worldwideweb.abilitypharma.com) comprised a News section. All the inventors of the present application have assigned all herein relevant rights to application of the present application and EP17382282.6 priority application dated 16 May 2017—said in other words, the below discussed webpage publication of the present applicant may be considered as so-called "inventor originated disclosure"—(i.e., the subject matter in the public disclosure must be attributable to the inventor, one or more co-inventors, or another who obtained the subject matter directly or indirectly from the inventor or co-inventor).

BACKGROUND ART

EP2409963B1 (Lipopharma-filed in 2010) describes use of 1,2-derivatives of polyunsaturated fatty acids (termed D-PUFAs) compounds for treatment of cancer.

The described fatty acids derivative compounds have the following formula:

$COOR_i$—$CHR_2$—$(CH_2)a$—$(CH=CH-CH_2)fc$--$(CH_2)c$-$CH_3$

An example of a preferred compound is:

$COOH$—$CHOH$—$(CH_2)_6$—$(CH=CH-CH_2)_2$—$(CH_2)_3$—$CH_3$(182A1)

The article "Erazo, et al.; Clinical Cancer Research; 22 (10) May 15, 2016" describes the above referred compound (182A1) in further details—in the article is this compound termed "ABTL081 2" and this term is used herein.

The article describes that ABTL081 2 induces autophagy-mediated cancer cell death without activating cellular apoptosis. The article reads:

[p 2515]:

"The majority of current anticancer treatments activate apoptosis, and resistance to chemotherapy is a major challenge in cancer (24). Autophagy-mediated cell death has emerged as an alternative to kill cancer cells without inducing resistance to apoptosis inducer drugs (25)."

[p 2517]:

"On the other hand, mTORCI activation is frequently associated with resistance to antitumor drugs (6). As ABTL081 2 is a potent inhibitor of the Akt/mTORC1 axis, its administration in combination with standard chemotherapeutic drugs might prove effective in therapy-resistant or apoptosis refractory tumor."

The News dated 22 Nov. 2016 reads:

"The Catalan biopharmaceutical company Ability Pharmaceuticals, SL announced today the initiation of its first Phase 2 Clinical Trial with its novel targeted anticancer agent ABTL081 2 to evaluate its efficacy and safety in combination with paclitaxel and carboplatin in 80 patients with advanced or recurrent endometrial cancer or squamous lung cancer as first-line therapy ( . . . )

In preclinical cancer models ABTL081 2 is efficacious as single agent with an excellent safety profile in a broad spectrum of cancer types: lung, endometrial, pancreatic cancer and neuroblastoma.

In these models, the compound has also synergistic effect with chemotherapy (taxanes, platinum compounds and gemcitabine) without increasing its toxicity."

The News dated Dec. 14, 2016 reads:

"In preclinical studies, ABTL081 2 have shown efficacy in pancreatic cancer as single agent and synergistic effect (by 8 to 90 times) in combination with taxanes, platinum compounds and gemcitabine, with induction of tumor regression without increasing the toxicity associated with chemotherapy ( . . . )

ABTL081 2 is currently in phase 2 as first-line therapy in combination with chemotherapy in patients with endometrial or squamous lung cancer."

With respect to use of the ABTL081 2 compound in combination with other chemotherapeutic agents—the above referred Erazo article and applicant (AbilityPharma) published News do not disclose any significant experimental data—i.e. the combination related statements may be seen as mere statements that are not supported by any significant verifiable experimental data.

The published News refers to phase II studies—as known in the art, the fact that phase II studies are running means that phase I studies are concluded and from this information, the skilled person can only conclude that the results on safety and tolerability in humans, as well as the pharmacokinetics studies, were positive—i.e. this provides no information about a possible therapeutic effect in human patients, in particular not about any possible combination synergistic effect. The skilled person only knows after the completion of the phase II trials an evaluation of the results whether the medicament is therapeutically effective—at the filing date of the present application was not published any herein relevant experimental data derived from phase II trials.

SUMMARY OF THE INVENTION

The problem to be solved by the present invention is to provide an improved treatment of cancer.

As discussed above, the compound $COOH$—$CHOH$—$(CH_2)_6$—$(CH=CH-CH2)2$-$(CH2)3$-$CH_3$ is herein termed ABTL081 2.

Working examples herein provides numerous detailed experimental data demonstrating significant synergistic effect in relation to use of the above discussed ABTL081 2 compound in combination with other chemotherapeutic agents.

As discussed in further details herein—the experimental data provided herein is based on established in vitro and in vivo (e.g. in mice) experimental tests-accordingly, based on the experimental data provided herein it is plausible/credible that herein relevant synergistic effects may be obtained in human cancer patients.

Example 4 herein discusses already obtained preliminary results from human critical trials—the already obtained human clinical trials are positive in the sense that these results indicate that there also in human is a synergistic effect in relation to use of the ABTL081 2 compound in combination with paclitaxel and carboplatin in patients with advanced endometrial cancer or squamous cell cancer.

Based on the knowledge of the prior art, the skilled person could not have foreseen with a reasonable expectation of success the herein experimentally described significant synergistic effects.

As discussed above with respect to the webpage disclosures of present applicant (AbilityPharma)—the combination related statements in these webpage disclosures may be seen as mere statements that are not supported by any significant verifiable experimental data—it is evident that based on these webpage disclosures it was not plausible/credible that herein relevant synergistic effects may be obtained in human cancer patients.

In short, working examples herein demonstrate among other issues the following:

Example 1:—In Vitro Experiments 1.1: ABTL081 2 and docetaxel have synergistic effect in vitro in a representative non-small cell lung adenocarcinoma cell line, where ABTL081 2 reduced more than 80-fold the $IC_{50}$ of docetaxel—i.e. a dramatically increased docetaxel cytotoxicity;

1.2: ABTL081 2 and paclitaxel have synergistic effect in vitro in 4 different lung carcinoma cell line, where ABTL081 2 reduced the $IC_{50}$ of paclitaxel in the range of 2 to 7-fold depending on the cell line. i.e an increased paclitaxel cytotoxicity;

1:3: ABTL081 2 and gemcitabine have synergistic effects in vitro in a representative pancreatic cancer cell line, where ABTL081 2 reduced 7-fold the $IC_{50}$ of gemcitabine—i.e. a dramatically increased gemcitabine cytotoxicity;

1:4: ABTL081 2 and carboplatin have synergistic effects in vitro in a representative endometrial cancer cell line, where ABTL081 2 reduced 3-fold the $IC_{50}$ of carboplatin—i.e. an increased carboplatin cytotoxicity; 1:5: ABTL081 2 and retinoic acid have synergistic effects in vitro in a representative neuroblastoma cancer cell line;

1:6: ABTL081 2 and paclitaxel have synergistic effects in vitro in a representative breast cancer cell line, where ABTL081 2 reduced 3-fold the $IC_{50}$ of paclitaxel—i.e. an increased paclitaxel cytotoxicity.

Example 2:—In Vivo Experiments 2.1: In a representative in vivo mice model, low doses of ABTL081 2 potentiated the lung cancer antitumor activity of Docetaxel with no negative toxic effect.

2.2: In a representative in vivo mice model, the combination of ABTL081 2+paclitaxel and carboplatin (P/C) treatment showed significant increase in the survival rate in a squamous cell cancer (SCC) model, with a 75% of survival at 20 days after treatments and comparted with 0% survival in ABTL081 2 and vehicle and 25% survival in P/C group.

2.3: In a representative in vivo mice model, the combination ABTL081 2+P/C showed a synergistic effect vs. the effect of each drug alone in relation to an adenocarcinoma lung cancer, as a significant tumor volume reduction was observed in animals treated with the combination vs. control and chemotherapy treated animals;

2.4: In a representative in vivo mice model, the combination ABTL081 2+pemetrexed and cisplatin showed a synergistic effect vs. the effect of chemotherapy alone in relation to an adenocarcinoma lung cancer, as a significant tumor volume reduction was observed in animals treated with the combination vs. control and chemotherapy treated animals;

2.5: In a representative in vivo mice model, the combination ABTL081 2+paclitaxel showed a synergistic effect vs. the effect of each drug alone in relation to endometrial cancer, as a significant tumor volume reduction was observed in animals treated with the combination vs. control animals;

2.6: In a representative in vivo mice model from a patient derived xenografts, the combination ABTL081 2+P/C showed a synergistic effect in relation to endometrial cancer, showing a significant higher tumor volume reduction compared to P/C, which also shows a significant tumor volume reduction compared to vehicle group during the first 47 days;

2.7: In a representative in vivo mice model, the combination ABTL081 2+Paclitaxel/Gemcitabine showed a synergistic effect in relation to pancreatic cancer, showing a significant higher tumor volume reduction compared to P/Gm alone. P/Gm also showed a higher tumor volume reduction compared to vehicle;

2.8: In a representative in vivo mice model, the combination ABTL081 2+Nab-Paclitaxel/Gemcitabine showed a synergistic effect in relation to pancreatic cancer, showing a significant higher tumor volume reduction compared to Nab-P/Gm alone. Nab-P/Gm also showed a higher tumor volume reduction compared to vehicle;

2.9: In a representative in vivo mice model, the combination ABTL081 2+cisplatin showed a synergistic effect in relation to neuroblastoma cancer, where the combination of ABTL081 2 with cisplatin results in stabilization of tumor progression for a longer period;

2.10: In a representative in vivo mice model, the combination ABTL081 2+doxorubicin showed a synergistic effect in relation to breast cancer, where the combination of ABTL0812 with paclitaxel showed a higher tumor volume reduction compared to vehicle.

The experimental data provided herein is based on established in vitro and in vivo (e.g. in mice) experimental tests-accordingly, based on the experimental data provided herein it is plausible/credible that herein relevant synergistic effects may be obtained in human cancer patients.

Examples of chemotherapeutic agents tested in working examples herein include:

Taxanes: Paclitaxel (Taxol), Nab-Paclitaxel (albumin bound Paclitaxel) and docetaxel;
Platinum-based agents: carboplatin and cisplatin;
Nucleotide analogs and precursor analogs: gemcitabine;
Folate antimetabolites: Pemetrexed;
Anthracyclines: Doxorubicin;
Accordingly, different groups/classes of chemotherapeutic agents have been tested and for all were demonstrated significant synergistic effect when used in combination with the ABTL0812 compound.

Based on the experimental data provided herein, it is plausible that herein positive synergistic effect would be obtainable by the majority of relevant chemotherapeutic agents.

As discussed above, the majority of current anticancer treatments activate apoptosis and all the above mentioned tested other chemotherapeutic agents activate apoptosis.

ABTL081 2 induces autophagy-mediated cancer cell death without activating cellular apoptosis. Experimental data provided herein demonstrate that ABTL0812 in combination with chemotherapeutics surprisingly may increase the level of apoptosis even though it is not the basic mechanism of ABTL0812.

Experimental data provided herein demonstrated for a chemotherapeutic agent (e.g. Docetaxel) essentially the following:

Docetaxel in amount giving 100% therapeutic effect=>results in a toxicity of Y.

Docetaxel in amount giving 50% therapeutic effect=>results in a reduced toxicity.

Docetaxel in an amount giving 50% therapeutic effect+ ABTL081 2 in an amount giving 50% therapeutic effect=>results in an effect 100% and toxicity is maintained at the same reduced level.

It was surprising for the present inventors that by combining with ABTL081 2 it was possible to significantly increase the effect of a chemotherapeutic agent (e.g. Docetaxel) without significantly increasing the toxicity.

The ABTL0812 compound is structurally and functionally similar to the other 1,2-derivatives of polyunsaturated fatty acids (D-PUFAs) compounds as described in above discussed EP2409963B1.

Accordingly, prima facie it is plausible that substantial all the fatty acids derivative compounds of EP2409963B1 would have a herein relevant synergistic effect in combination with a chemotherapeutic agent.

Accordingly, a first aspect of the invention relates to a pharmaceutical combination comprising:

(A): a compound which is a polyunsaturated fatty acid of formula $COORi\text{-}CHR_2\text{-}(CH_2)a(CH\text{=}CHCH2)b\text{-}(CH_2)c\text{-}Cl\text{-}I3$, a pharmaceutically acceptable salt thereof, or a combination thereof, wherein
  (i) a can be any integer value between 0 and 7,
  (ii) b can be any integer value between 2 and 7,
  (iii) c can be any integer value between 0 to 7,
  (iv) $R_1$ is H, Na, K, $CH_3$, $CH_3\text{—}CH_2$, or $PO(0\text{-}CH_2\text{—}CH_3)_2$, and
  (v) $R_2$ is OH, $OCH_3$, O—$CH_3COOH$, $CH_3$, Cl, $CH_2OH$, $OPO(0\text{-}CH_2\text{—}CH_3)_2$, NOH, F, HCOO or $N(OCH_2CH_3)_2$;
and
(B): a chemotherapeutic agent compound for the simultaneous, separate or sequential use in the treatment of a cancer in a human patient.

As understood by the skilled person in the present context—the chemotherapeutic agent of Compound (B) of the first aspect is of course not a compound within the scope of Compound (A) of the first aspect.

As understood by the skilled person in the present context—in relation to the herein discussed combination treatment it is not essential if the two compounds (A) and (B) are administrated e.g. simultaneously as a single composition or e.g. sequentially as two separate compositions. The important matter is that an effective amount of the compound/ agent first administered is in the patient's body when the second compound/agent is administered.

Accordingly, the term "combination" of the first aspect relates herein to the various combinations of compounds (A) and (B), for example in a single pharmaceutical composition, in a combined mixture composed from separate pharmaceutical formulations/compositions of the single active compounds, such as a "tank-mix", and in a combined use of the single active ingredients when applied in a sequential manner, i.e. one after the other with a reasonably short period, such as a few hours or days or in simultaneous administration. The order of applying the compounds (A) and (B) is not essential.

A combination of the compounds (A) and (B) can be formulated for its simultaneous, separate or sequential administration. Particularly, if the administration is not simultaneous, the compounds are administered in a relatively close time proximity to each other. Furthermore, compounds are administered in the same or different dosage form or by the same or different administration route, e.g. one compound can be administered topically and the other compound can be administered orally. The combination of the two compounds can e.g. be administered:

as a combination that is being part of the same medicament formulation, the two compounds being then administered always simultaneously;

as a combination of two units/compositions, each with one of the substances giving rise to the possibility of simultaneous, sequential or separate administration;

For instance, the compound (A) is independently administered from the compound (B) (i.e. in two units) but at the same time.

In another suitable example, the compound (A) is administered first and then the compound (B) is separately or sequentially administered-alternatively, the compound (B) is administered first and then the compound (A) is separately or sequentially administered.

The term "pharmaceutical" e.g. in relation to a "pharmaceutical composition" shall be understood according to the art—i.e. that it refers to a preparation/composition which is in such form as to permit the biological activity of the active ingredients to be effective, and physiologically tolerable, that is, which contains no additional components which are unacceptably toxic to a subject to which the composition would be administered. Particularly, the term "pharmaceutically acceptable" means it is approved by a regulatory agency of a state or federal government or is included in the U.S. Pharmacopoeia or other generally recognized pharmacopoeia for use in animals, and more particularly in humans.

Embodiment of the present invention is described below, by way of examples only.

A combination of a herein described preferred embodiment with another herein described preferred embodiment is an even more preferred embodiment.

DRAWINGS

FIG. 1: ABTL081 2 shows in vitro synergy with docetaxel in A549 human lung adenocarcinoma cell line. Cytotoxicity of ABTL081 2, docetaxel and the combination of both drugs. A potentiation of docetaxel cytotoxicity can be observed, as its $IC_{50}$ was reduced 86 times when a low concentration (approximately half of its $IC_{50}$) of ABTL081 2 was added. Results show the average of two independent experiments. See working Example herein for further details.

Figure 2:
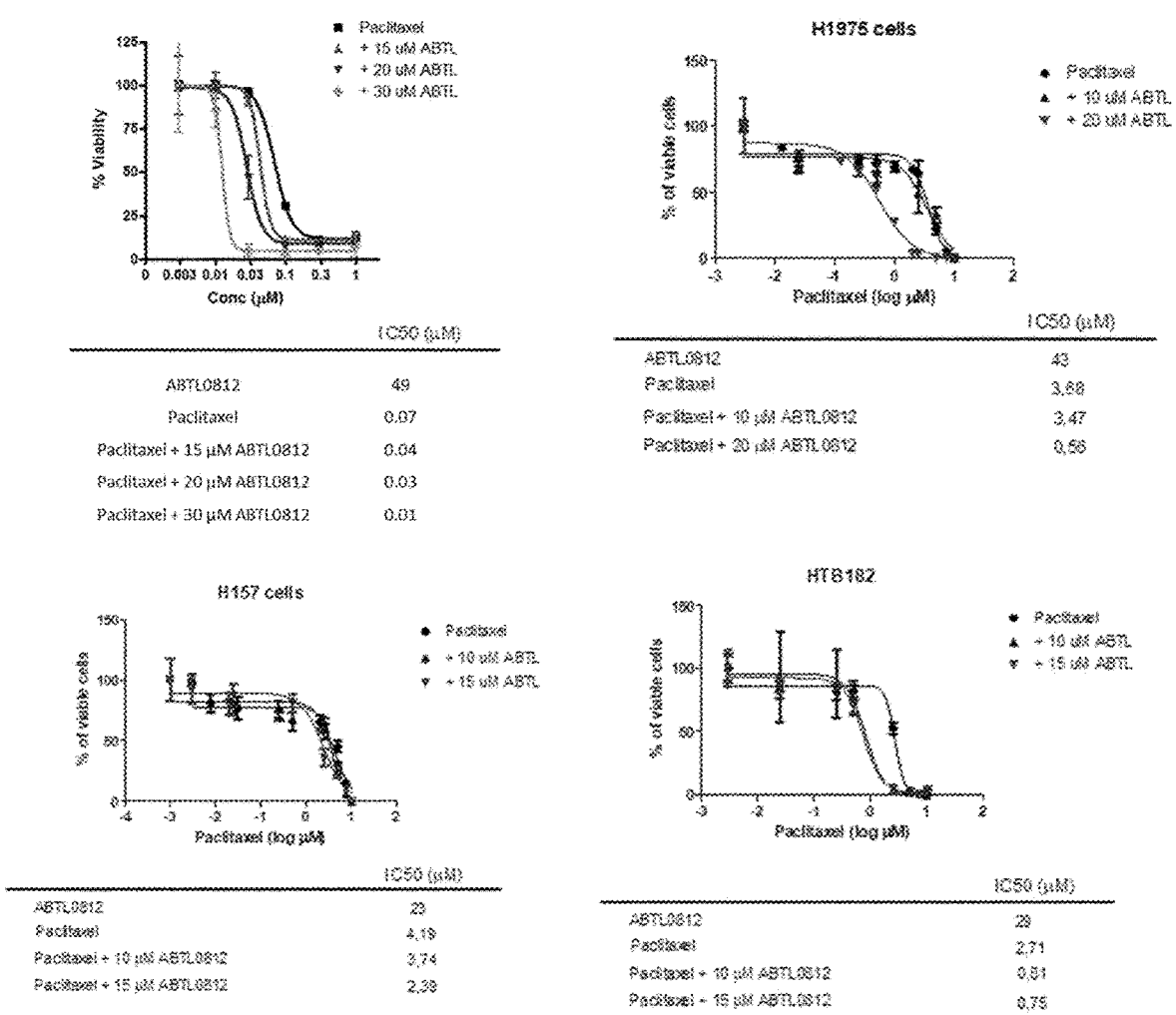
Figure 3:
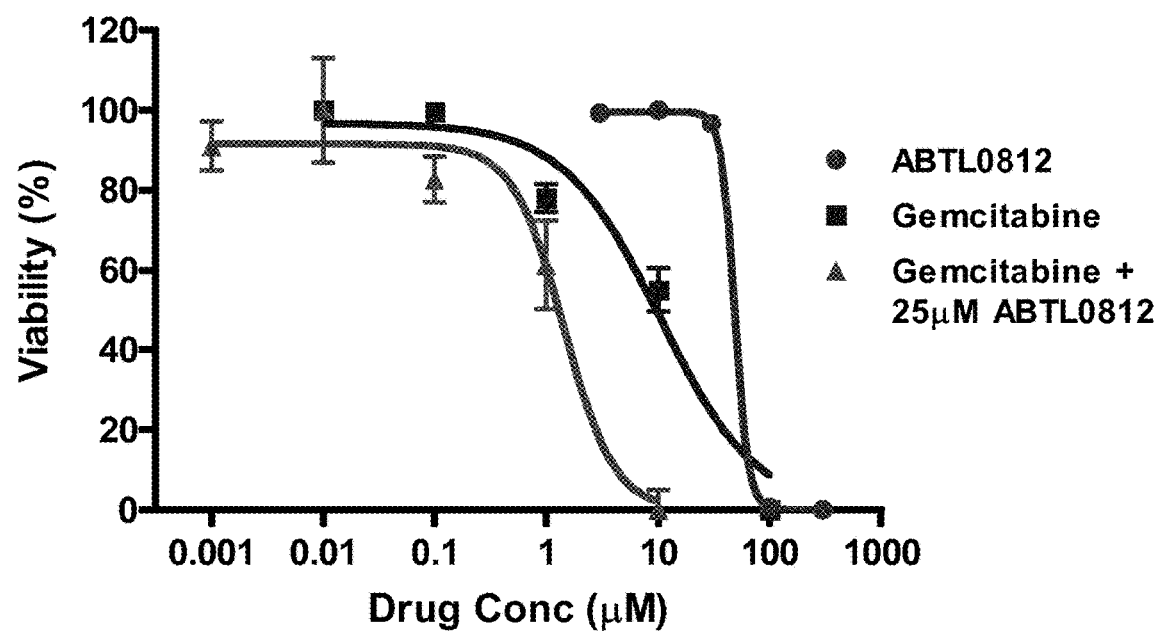

FIG. 2: ABTL081 2 shows in vitro synergy with paclitaxel in A549 and H1975 human lung adenocarcinoma cell lines and in H157 and HTB182 human squamous lung cancer cell lines. Cytotoxicity of ABTL081 2, paclitaxel and the combination of both drugs in all four different lung cancer cell lines. A potentiation of paclitaxel cytotoxicity can be observed in all four cell lines as its $IC_{50}$ was reduced in the range of 2 to 7-fold depending on the cell line when a low concentration (approximately half of its $IC_{50}$) of ABTL081 2 was added. Results show the average of two independent experiments for each cell line. See working Example herein for further details FIG. 3: ABTL081 2 shows in vitro synergy with gemcitabine in MiaPaca2 human pancreatic cancer cell line. Cytotoxicity of ABTL081 2, gemcitabine and the combination of both drugs. A potentiation of gemcitabine cytotoxicity can be observed in the presence of ABTL081 2, as its $IC_{50}$ was reduced by 7-fold when a low concentration (approximately half of its $IC_{50}$) of ABTL081 2 was added. Results show the average of two independent experiments. See working Example herein for further details.

Figure 4:
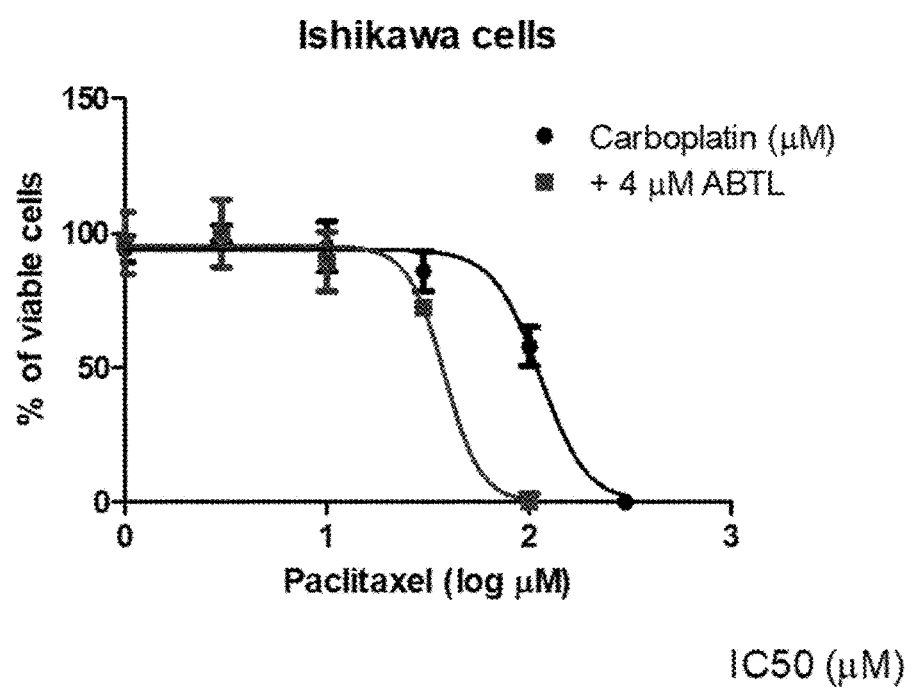
Figure 5:
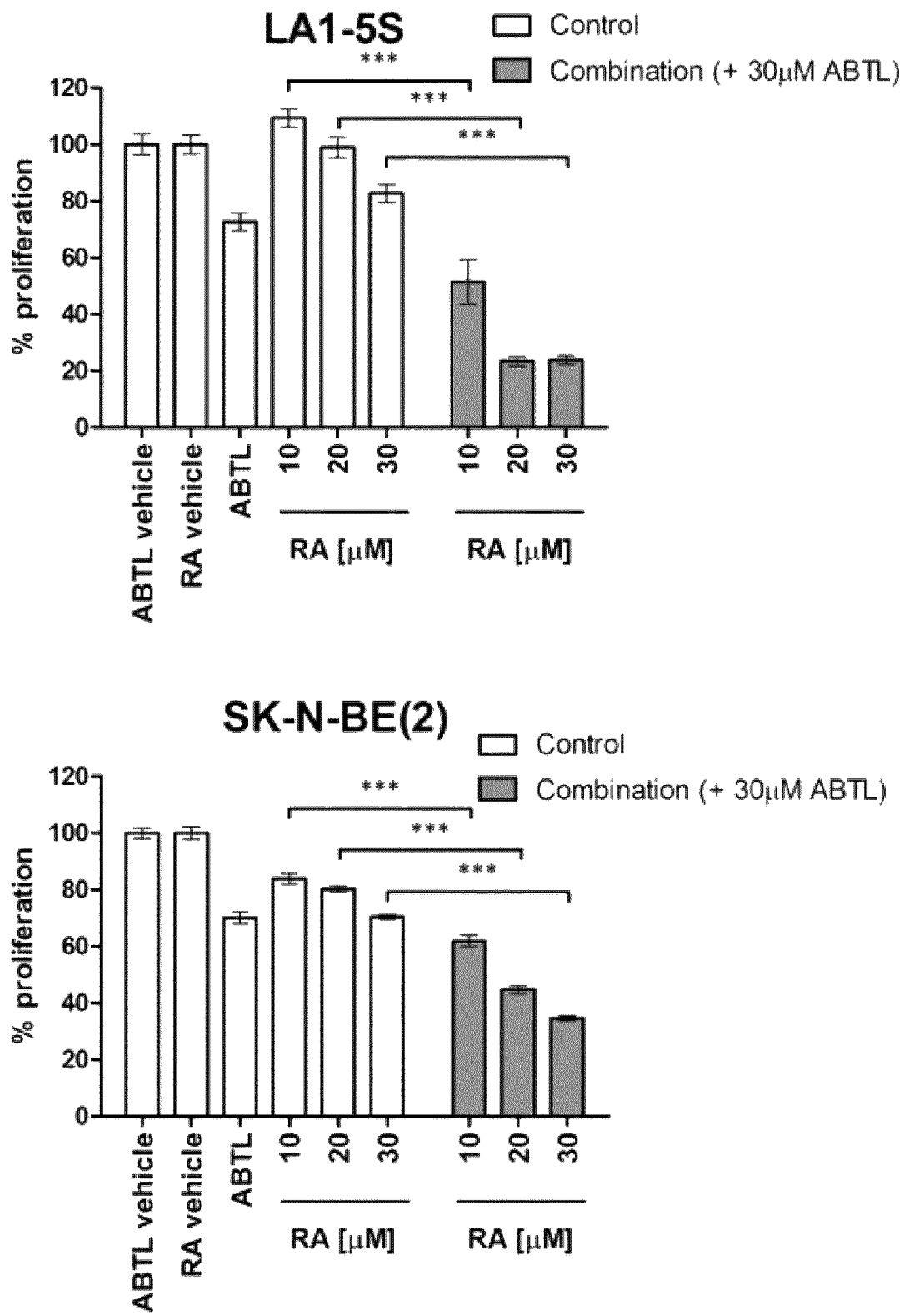

FIG. 4: ABTL081 2 shows in vitro synergy with carboplatin in Ishikawa human endometriaol cancer cell line. Cytotoxicity of ABTL081 2, carboplatin and the combination of both drugs. A potentiation of docetaxel cytotoxicity can be observed, as its $IC_{50}$ was reduced 3 times when a low concentration (approximately half of its $IC_{50}$) of ABTL081 2 was added. Results show the average of two independent experiments. See working Example herein for further details FIG. 5: ABTL081 2 shows in vitro synergy with retinoic acid in LAI-5S and SK-N-BE (2) human neuroblastoma cell lines. Cytotoxicity of ABTL081 2, retinoic acid and the combination of both drugs. A potentiation of retinoic acid (RA) cytotoxicity can be observed in both cell lines, as cell viability with RA was reduced from 82.8% to 23.8% in LAI-5S cell and from 70.4% to 34.7% in SK-N-BE (2) cells when RA was incubated with a low concentration (approximately half of its $IC_{30}$) of ABTL081 2. Results show the average of two independent experiments. See working Example herein for further details.

Figure 6:
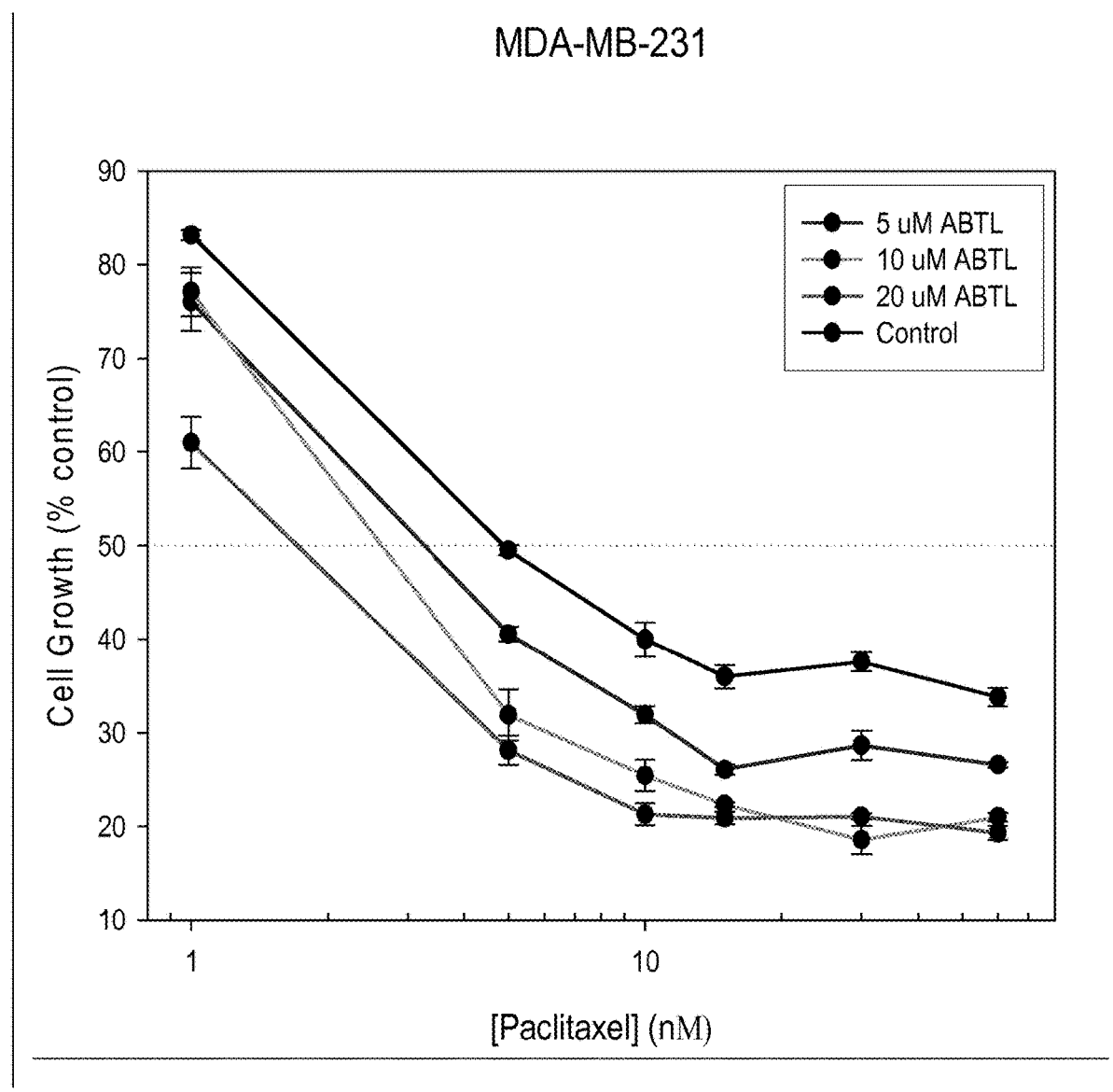

FIG. 6: ABTL081 2 shows in vitro synergy with paclitaxel in MDA-DB-231 human triple negative breast cancer cell line. Cytotoxicity of ABTL081 2, paclitaxel and the combination of both drugs. A potentiation of paclitaxel cytotoxicity can be observed, as its $IC_{50}$ was reduced 2.7 times when low concentrations (below its $IC_{50}$) of ABTL081 2 were added. Results show the average of two independent experiments. See working Example herein for further details.

Figure 7:
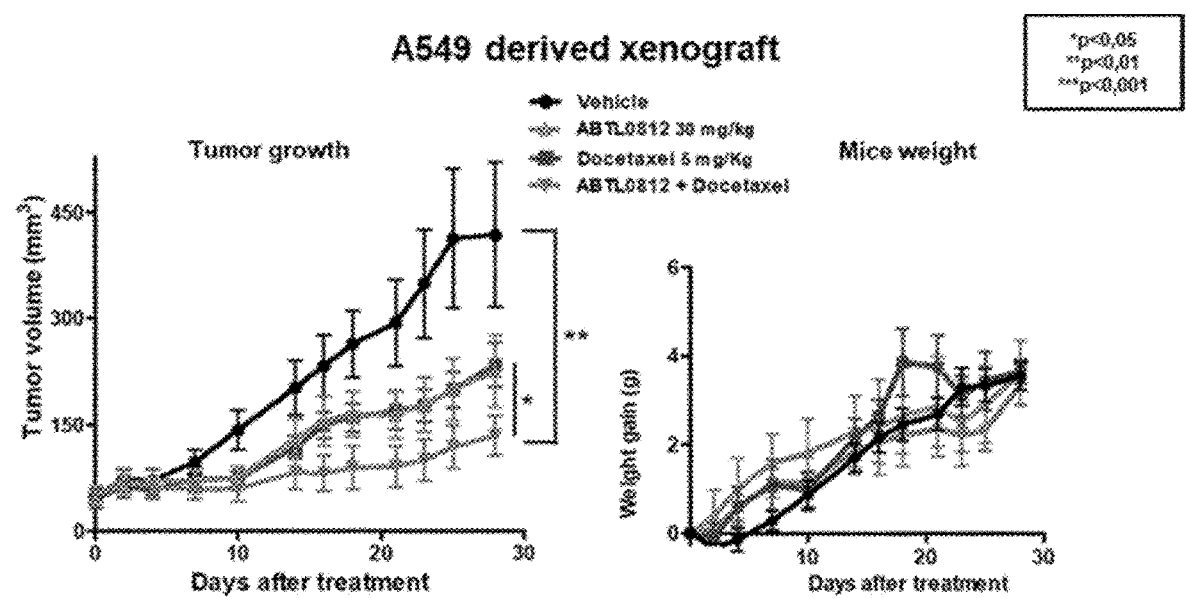

FIG. 7: ABTL081 2 shows potentiation of docetaxel therapeutic effect without increased toxicity in an in vivo A549 human lung adenocarcinoma xenograft model. Left: Anti-tumor effect of the combination of ABTL081 2 with docetaxel in a549 human lung adenocarcinoma xenograft model, showing a significant decrease in tumor growth compared with ABTL081 2, docetaxel and vehicle groups. p values are measured between ABTL081 2+docetaxel vs docetaxel and vs vehicle. Right: Total body weight in the different treatment groups during the whole experimental period. See working Example herein for further details.

Figure 8:
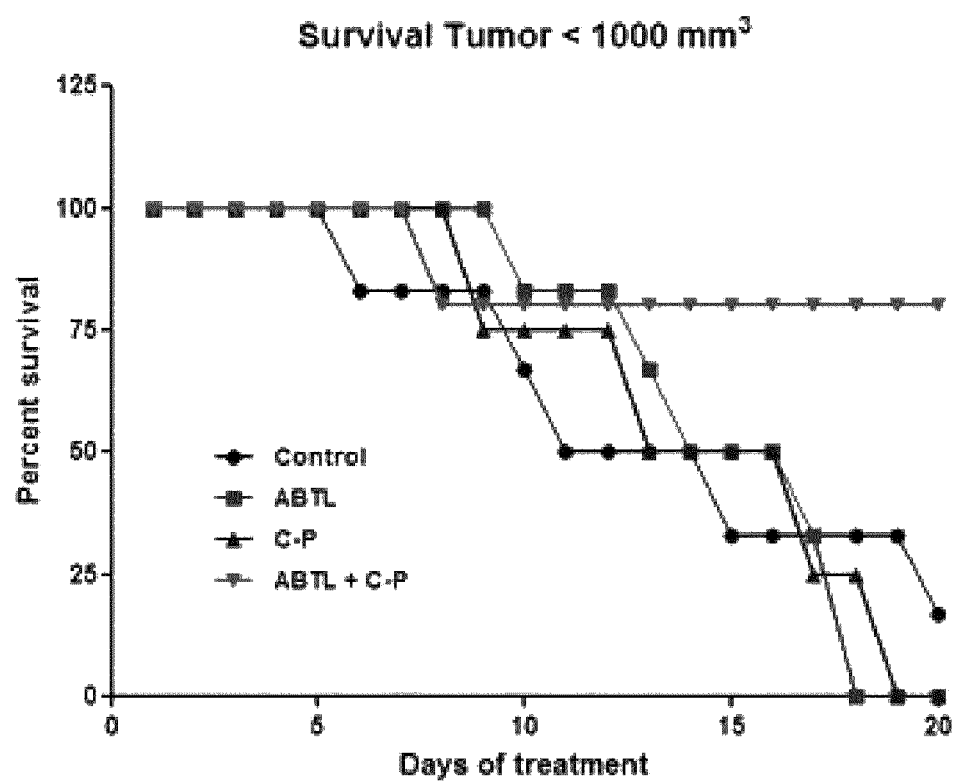

FIG. 8: ABTL081 2 shows potentiation of paclitaxel/carboplatin (P/C) therapeutic effects, without increased toxicity in an in vivo H157 human squamous lung cancer xenograft model. Kaplan-Meier plot from H157 xenograft treated with ABTL081 2, P/C, ABTL081 2+P/C and vehicle, where ABTL081 2+P/C shows the highest survival rate. See working Example herein for further details.

Figure 9:
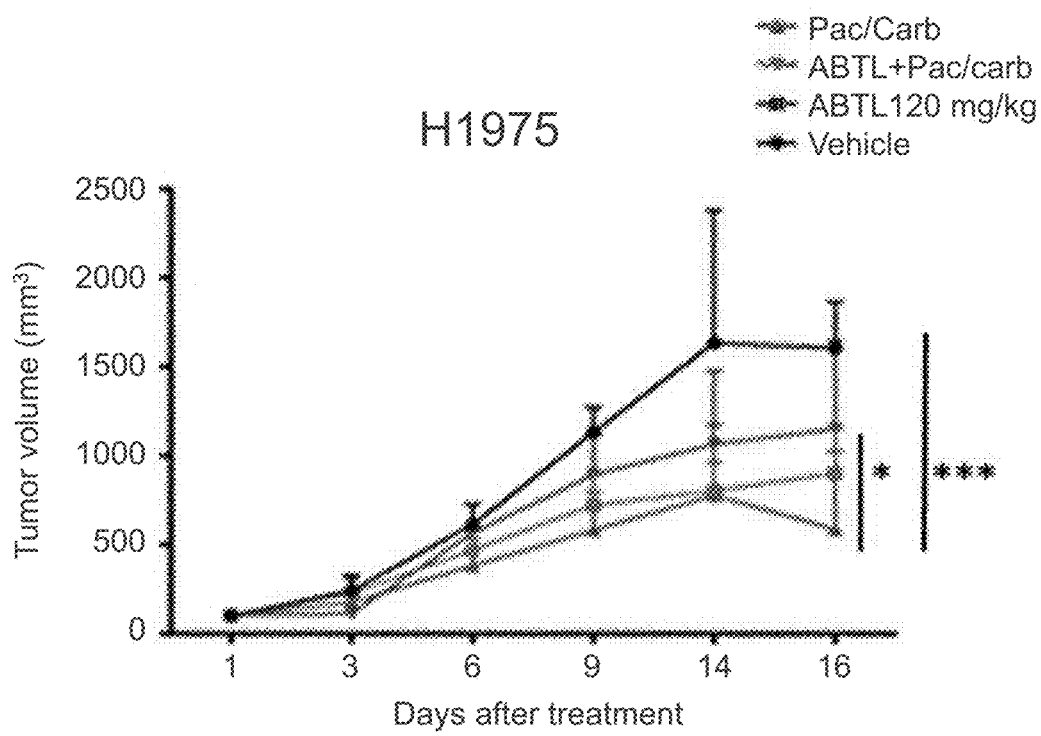
Figure 9:
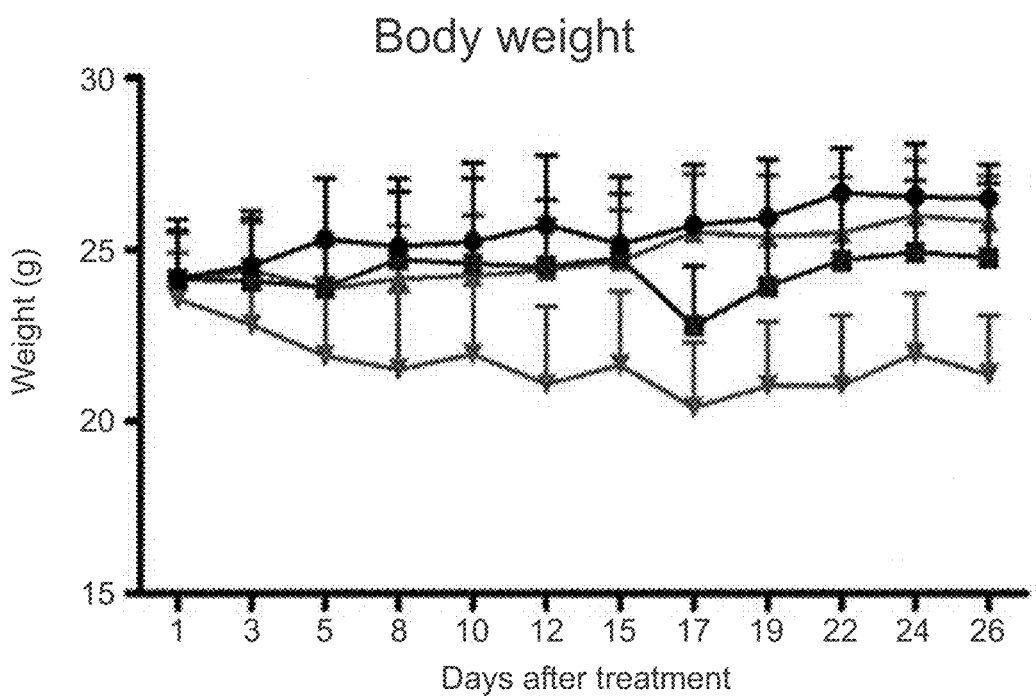

FIG. 9: ABTL081 2 shows potentiation of P/C therapeutic effects, without increased toxicity in an in vivo H1975 human lung adenocarcinoma xenograft model. Left: Anti-tumor effect of the combination of ABTL081 2 with P/C in H1975 human lung adenocarcinoma xenograft model, showing the highest tumor volume reduction compared with P/C, ABTL081 2 or vehicle groups. p values are measured between ABTL081 2+P/C vs P/C and vs vehicle. Right: Total body weight in the different treatment groups during the whole experimental period. See working Example herein for further details.

Figure 10:
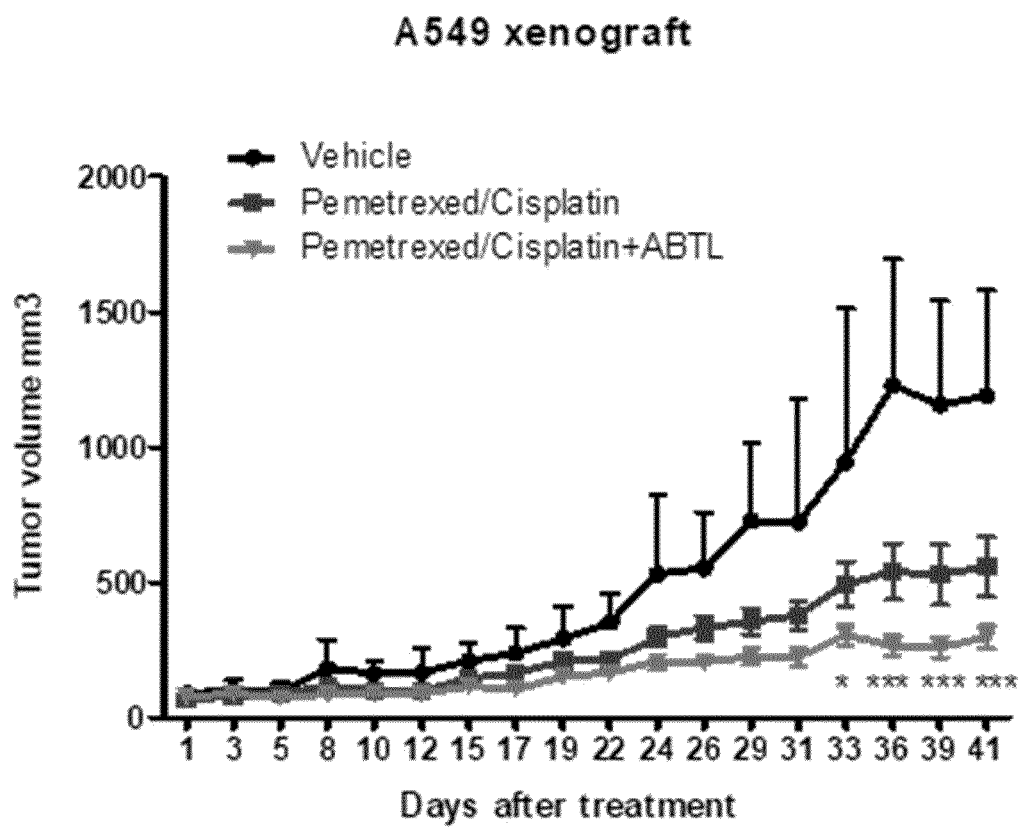
Figure 10:
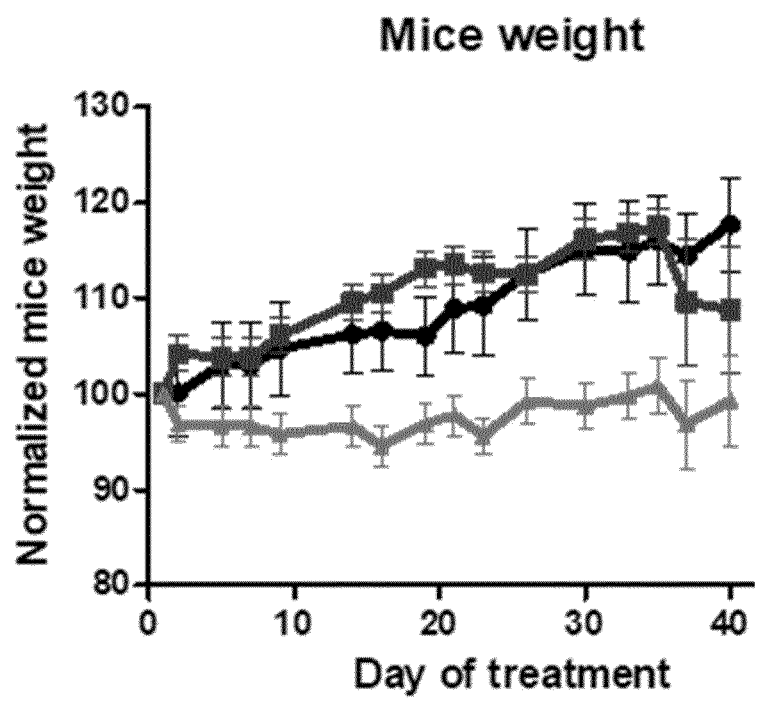

FIG. 10: ABTL081 2 shows potentiation of pemetrexed and cisplatin therapeutic effects, without increased toxicity in an in vivo A549 human lung adenocarcinoma xenograft model. Left: Anti-tumor effect of the combination of ABTL081 2 with pemetrexed and cisplatin that shows a significant decrease in tumor growth compared with pemetrexed and cisplatin and vehicle groups. p values are measured between ABTL081 2+pemtrexed and cisplatin vs vehicle. Right: Total body weight in the different treatment groups during the whole experimental period. See working Example herein for further details.

Figure 11:
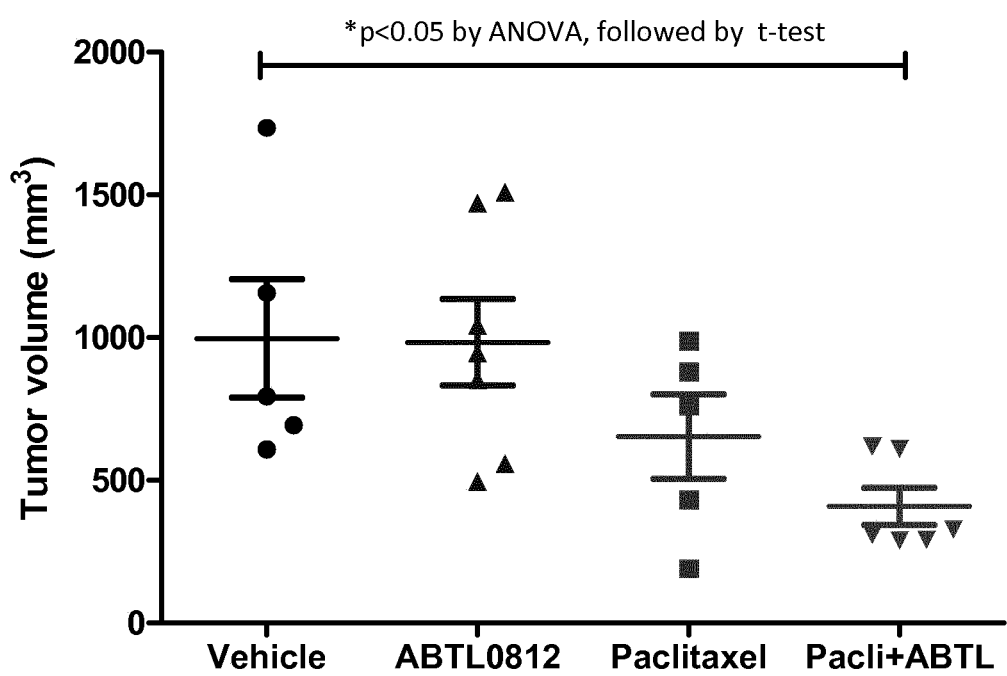

FIG. 11: ABTL081 2 shows potentiation of paclitaxel therapeutic effects, without increased toxicity in an in vivo Ishikawa human endometrial cancer xenograft model implanted orthotopically. Left: animals were sacrificed after three weeks of treatment, tumors excised, and tumor volume determined. A significant statistical reduction was observed in animals that received the combination ABTL081 2+paclitaxel vs. control animals that received vehicle only. p values are measured between ABTL081 2+paclitaxel vs vehicle. Right: Total body weight in the different treatment groups during the whole experimental period See working Example herein for further details.

Figure 12:
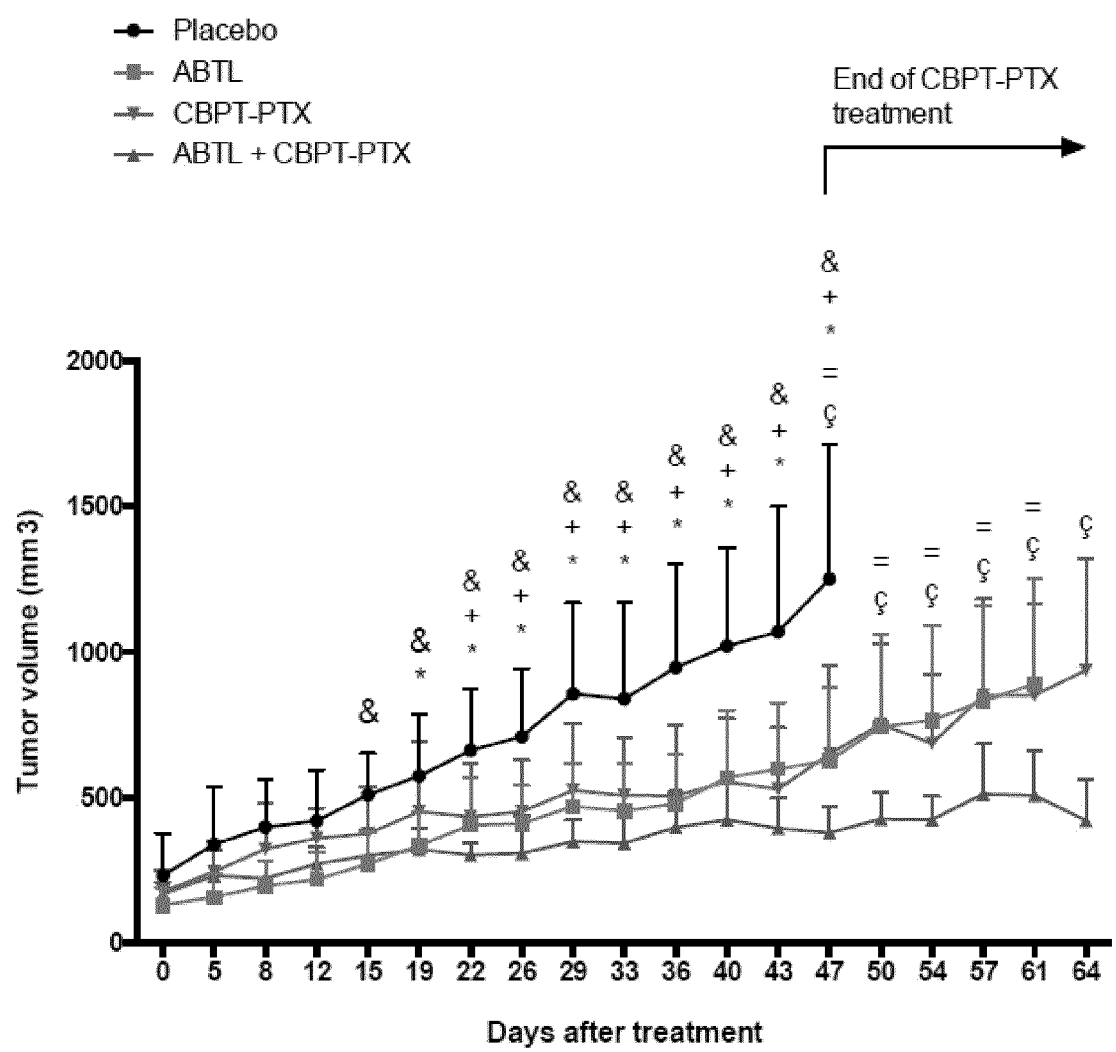

FIG. 12: ABTL081 2 shows potentiation of P/C therapeutic effects, without increased toxicity, in an in vivo human endometrial cancer patient derived xenografts. Figure left: A piece of tumor surgically removed from a patient with serous histology, grade IIIC2, 100% of myometrial invasion and pelvic and aortic lymph node and lymph vascular space invasion and carrying mutations in p53 and PI3KCA gene was implanted in nude mice. ABTL081 2 in combination with P/C shows significant reduction in tumor compared with P/C, ABTL081 2 and vehicle. Figure p values are indicated in the figure. Right: Total body weight for the different treatment groups during the whole experimental period are shown below. See working Example herein for further details.

Figure 13:
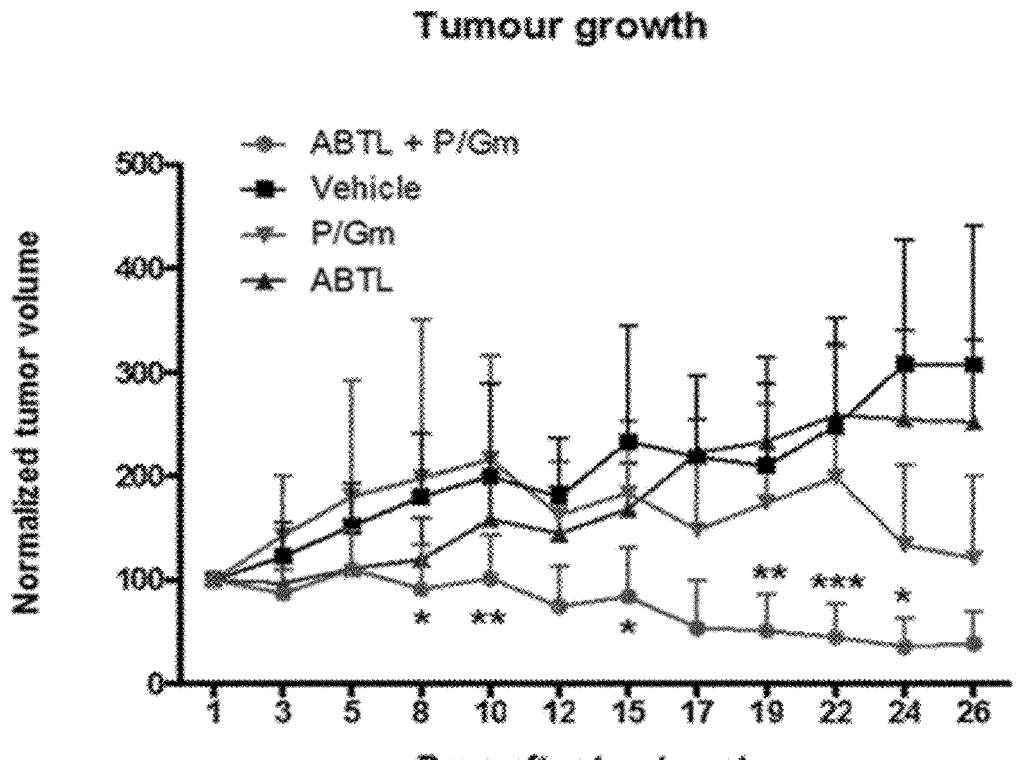
Figure 13:
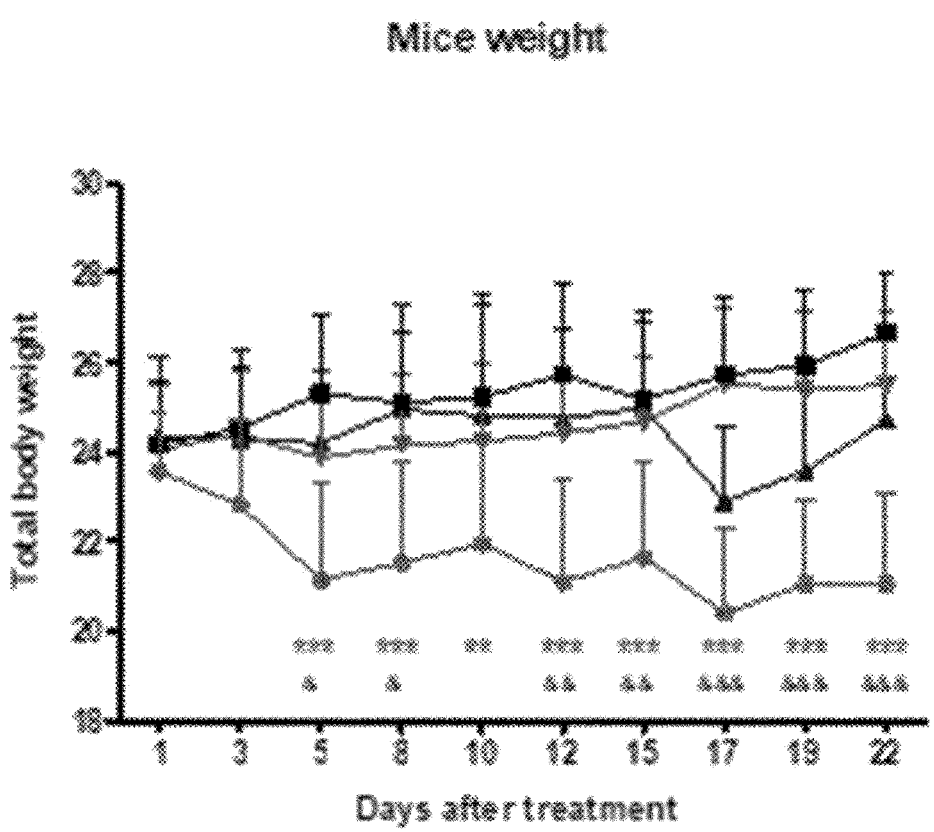

FIG. 13: ABTL081 2 shows potentiation of gemcitabine and paclitaxel (Gm/P) without increased toxicity, in an in vivo MiaPAca2 human pancreatic cancer xenograft model Left: Anti-tumor effect of the combination of ABTL081 2+Gem/P showing the highest tumor volume reduction compared with Gm/P, ABTL081 2 or vehicle. p values are measured between ABTL081 2+gemcitabine and paclitaxel vs gemcitabine and paclitaxel, vs gemcitabine and vs vehicle Right: Total body weight in the different treatment groups during the whole experimental period. See working Example herein for further details.

Figure 14:
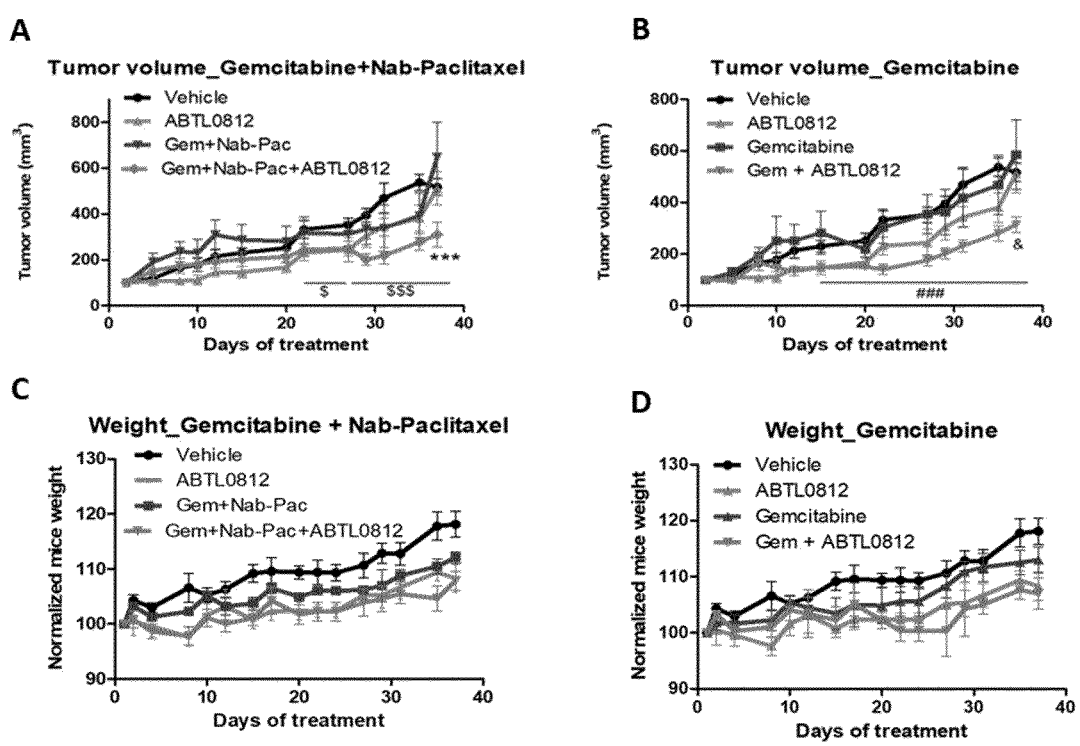

FIG. 14: ABTL081 2 shows potentiation of gemcitabine (Gm) alone, and potentiation of gemcitabine with Nab-Paclitaxel (Gm/Nab-P) without increased toxicity, in two in vivo MiaPAca2 human pancreatic cancer xenograft models Left: Anti-tumor effect of the combination of ABTL081 2+Gm/Nab-P showing the highest tumor volume reduction compared with Gm/Nab-P, ABTL081 2 or vehicle. Right; anti-tumor effect of the combination of ABTL081 2+Gm showing the highest tumor volume reduction compared with Gm, ABTL081 2 or vehicle. p values are measured between ABTL081 2+Gm/Nab-P and ABTL081 2+Gm vs vehicle. Total body weight for the different treatment groups during the whole experimental period are shown below See working Example herein for further details.

Figure 15:
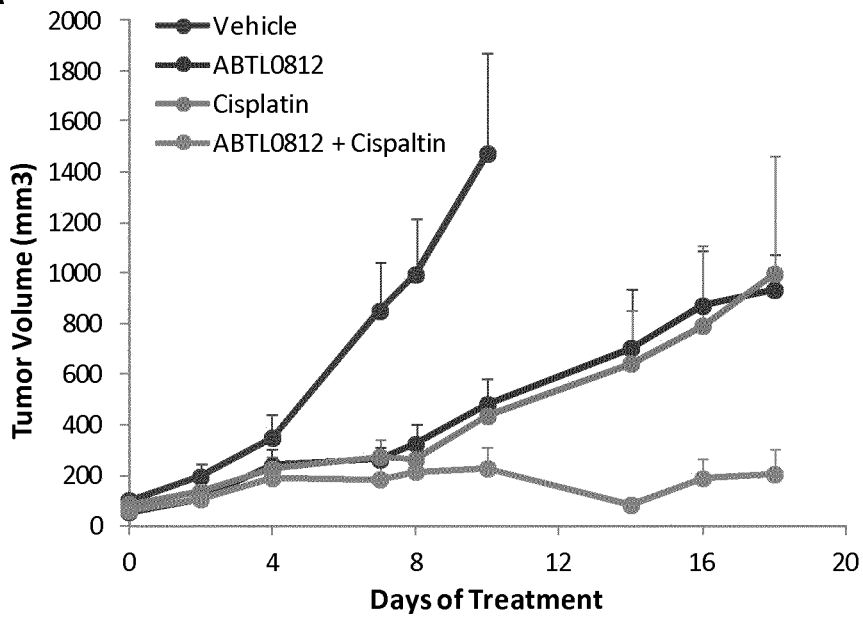
Figure 15:
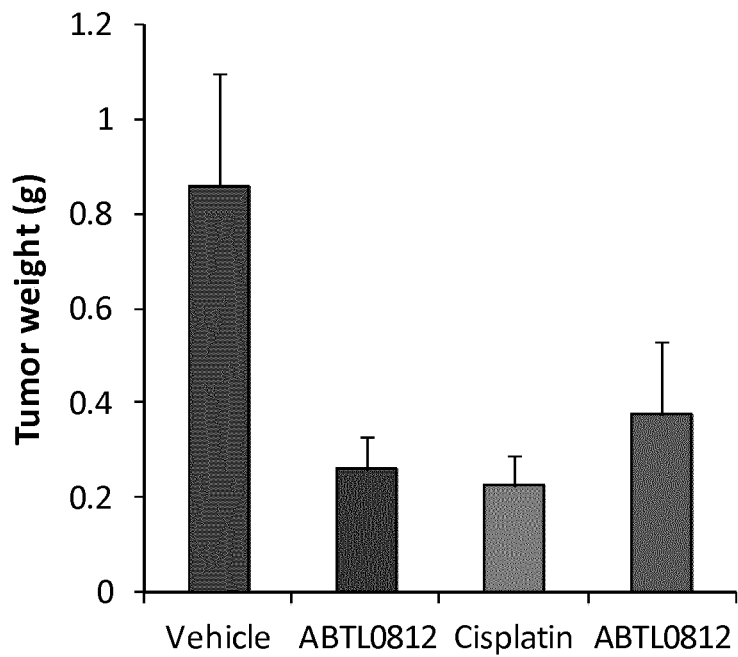

FIG. 15: ABTL081 2 shows potentiation of cisplatin therapeutic effect without increasing toxicity in an in vivo SH-SY5Y human neuroblastoma xenograft model. Left: Anti-tumor effect of the combination of ABTL081 2+cisplatin, showing the highest tumor volume reduction compared with ABTL081 2, cisplatin or vehicle. At day 10, animals in the control group had to be sacrificed, in parallel, half of the animals in the treatment groups were also sacrificed, while the rest were studied for a longer period. Left: Tumor weight at sacrifice after 10 days of treatment (p<0.05 by t-test). See working Example herein for further details.

Figure 16:
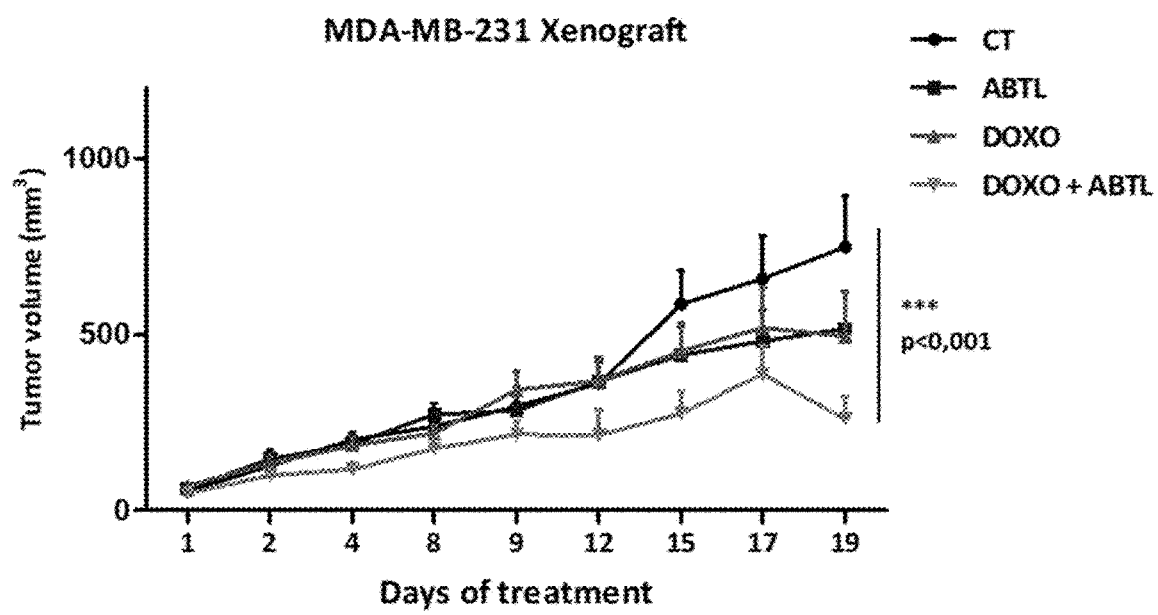
Figure 16:
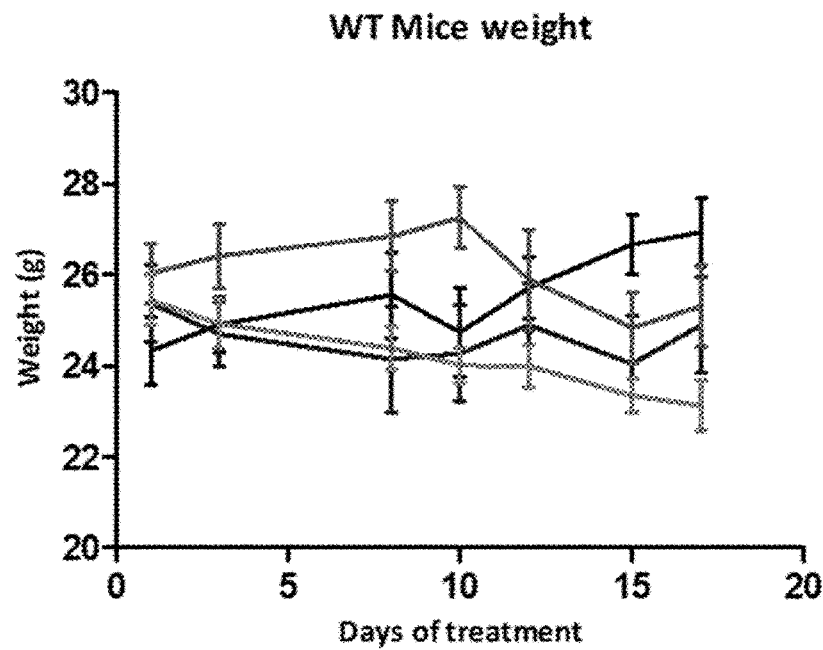

FIG. 16: ABTL081 2 shows potentiation of doxorubicin therapeutic effects, without increased toxicity in an in vivo MDA-DB-231 human triple negative breast cancer xenograft model. Left: Anti-tumor effect of the combination of ABTL081 2+doxorubicin showing the highest tumor volume reduction compared with doxorubicin, ABTL081 2 or vehicle. p values are measured between ABTL081 2+doxorubicin vs vehicle. Right: Total body weight in the different treatment groups during the whole experimental period See working Example herein for further details.

Figure 17:
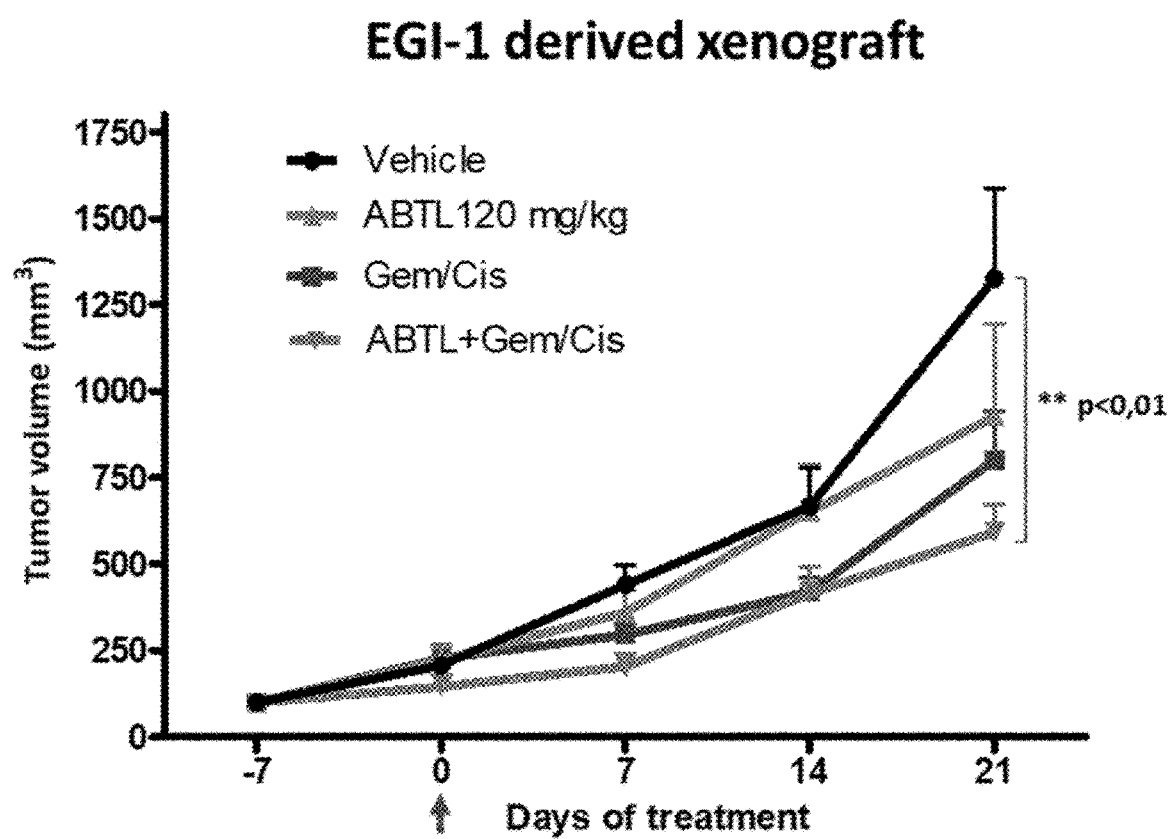

FIG. 17: ABTL081 2 shows potentiation of gemcitabine and cisplatin (Gm/Cis) therapeutic effects, without increased toxicity in an in vivo EGI-1 human cholangiocarcinoma xenograft model. Left: Anti-tumor effect of the combination of ABTL081 2+Gm/Cis showing the highest tumor volume reduction compared with Gm/Cis, ABTL081 2 or vehicle p values are measured between ABTL081 2+Gm/Cis vs vehicle. Right: Total body weight in the different treatment groups during the whole experimental period See working Example herein for further details.

DETAILED DESCRIPTION OF THE INVENTION

Compound (A) of the First Aspect

A preferred embodiment is wherein
(i) a can be any integer value between 5 and 7,
(ii) b can be any integer value between 2 and 4,
(iii) c can be any integer value between 1 to 5.

Preferably, $R_1$ may be H, Na, K, $CH_3$, $CH_3$—$CH_2$, or $PO(0\text{-}CH_2\text{—}CH_3)_2$, Preferably $R_2$ may be OH, $OCH_3$, $0\text{-}CH_3COOH$, $CH_3$, Cl, $CH_2OH$, $OPO(0\text{-}CH_2\text{—}CH_3)_2$, NOH, F, HCOO or $N(OCH_2CH_3)_2$.

In a preferred embodiment $R_1$ is H and $R_2$ is OH.

In another preferred embodiment $R_1$ is Na and $R_2$ is OH.

Preferably, Compound (A) is at least one compound selected from the group consisting of:

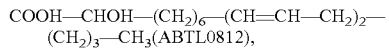
COOH—CHOH—(CH$_2$)$_6$—(CH=CH—CH$_2$)$_2$—(CH$_2$)$_3$—CH$_3$(ABTL0812),

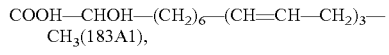
COOH—CHOH—(CH$_2$)$_6$—(CH=CH—CH$_2$)$_3$—CH$_3$(183A1),

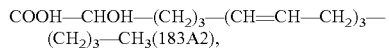
COOH—CHOH—(CH$_2$)$_3$—(CH=CH—CH$_2$)$_3$—(CH$_2$)$_3$—CH$_3$(183A2),

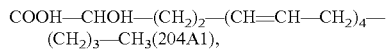
COOH—CHOH—(CH$_2$)$_2$—(CH=CH—CH$_2$)$_4$—(CH$_2$)$_3$—CH$_3$(204A1),

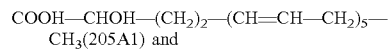
COOH—CHOH—(CH$_2$)$_2$—(CH=CH—CH$_2$)$_5$—CH$_3$(205A1) and

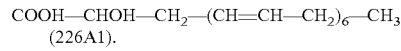
COOH—CHOH—CH$_2$—(CH=CH—CH$_2$)$_6$—CH$_3$ (226A1).

Most preferably, Compound (A) is COOH—CHOH—(CH$_2$)$_6$—(CH=CH—CH$_2$)$_2$—(CH$_2$)$_3$—CH$_3$ (ABTL081 2).

A pharmaceutically acceptable salt of Compound (A) refers to any pharmaceutically acceptable salt of Compound (A). As known in the art, there are numerous known pharmaceutically acceptable salts. Examples of pharmaceutically acceptable salts include, but are not limited to, sodium (Na), potassium, acetates, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formales, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phenylbutyrates, citrates, lactates, gammahydroxybutyrates, glycollates, tartarates, alkanesulfonates (e.g. methane-sulfonate or mesylate), propanesulfonates, naphthalene-1-sulfonates, naphthalene-2-sulfonates, and mandelates. In a particular embodiment, the salt of Compound (A) is the sodium salt.

As understood by the skilled person in the present context, when there herein is referred to a preferred formula of Compound (A), such as e.g. ABTL081 2—it is herein understood that it also included as salt thereof—for instance, when there herein is referred to that Compound (A) is COOH—CHOH—(CH$_2$)$_6$—(CH=CH—CH$_2$)$_2$—(CH$_2$)$_3$—CH$_3$ (ABTL081 2) then there is also referred to a salt of ABTL081 2.

Preferably, Compound (A) is a sodium salt of COOH—CHOH—(CH$_2$)$_6$—(CH=CH—CH$_2$)$_2$—(CH$_2$)$_3$—CH$_3$ (ABTL081 2).

Compound (B) of the First Aspect

Preferably, Compound (B) is at least one chemotherapeutic agent compound selected from the group consisting of:

Bifunctional Alkylator (preferably Cyclophosphamide, Mechlorethamine, Chlorambucil or Melphalan);

Monofunctional Alkylator (preferably Dacarbazine (DTIC), Nitrosoureas or Temozolomide); Anthracycline (preferably Daunorubicin, Doxorubicin, Epirubicin, Idarubicin, Mitoxantrone or Valrubicin);

Taxane (preferably Paclitaxel, Docetaxel, Nab-Paclitaxel or Taxotere);

Epothilone (preferably patupilone, sagopilone or ixabepilone);

Deacetylase Inhibitor (preferably Vorinostat or Romidepsin);

Inhibitor of Topoisomerase I (preferably Irinotecan or Topotecan);

Inhibitor of Topoisomerase II (preferably Etoposide, Teniposide or Tafluposide);

Kinase inhibitor (preferably Bortezomib, Erlotinib, Gefitinib, Imatinib, Vemurafenib or Vismodegib);

Nucleotide analog and/or precursor analog (preferably Azacitidine, Azathioprine, Capecitabine, Cytarabine, Doxifluridine, Fluorouracil, Gemcitabine, Hydroxyurea, Mercaptopurine, Methotrexate or Tioguanine);

Peptide antibiotic (preferably Bleomycin or Actinomycin);
Platinum-based agent (preferably Carboplatin, Cisplatin or Oxaliplatin);
Retinoid (preferably Tretinoin, Alitretinoin or Bexarotene); and
Vinca alkaloid and derivative (preferably Vinblastine, Vincristine, Vindesine or Vinorelbine).

As understood in the present context—in relation to any of the preferred listed examples of Compound (B) is it most preferred that Compound (A) is COOH—CHOH—$(CH_2)_6$—$(CH=CH—CH_2)_2$—$(CH_2)_3$—$CH_3$ (ABTL081 2).

More preferably, Compound (B) is at least one chemotherapeutic agent compound selected from the group consisting of:
Cyclophosphamide;
Melphalan;
Docetaxel;
Paclitaxel;
Nab-paclitaxel;
Carboplatin;
Cisplatin;
Oxaliplatin;
Methotrexate
Pemetrexed;
Azathioprine;
Capecitabine;
Fluouracil;
Mercaptopurine;
Gemcitabine;
Bleomcycin;
Actinomycin;
Vincristine;
Vinblastine;
Vinorelbine;
Retinoic acid;
Temozolomide;
Daunorubicin
Doxorubicin;
Irinotecan; and
Topotecan.

Even more preferably, Compound (B) is at least one chemotherapeutic agent compound selected from the group consisting of:
Docetaxel;
Paclitaxel;
Nab-paclitaxel;
Carboplatin;
Cisplatin;
Oxaliplatin;
Methotrexate
Pemetrexed;
Gemcitabine;
Bleomycin
Retinoic acid;
Temozolomide;
Doxorubicin;
Irinotecan; and
Topotecan.

It may be preferred that Compound (B) of the first aspect comprises two or more different chemotherapeutic agents (in particular when Compound (A) is COOH—CHOH—$(CH_2)_6$—$(CH=CH—CH_2)_2$—$(CH_2)_3$—$CH_3$ (ABTL081 2))—such as preferably wherein Compound (B) of the first aspect comprises:
Paclitaxel and Carboplatin;
Paclitaxel and Gemcitabine;
Nab-Paclitaxel and Gemcitabine;
Gemcitabine and Cisplatin;
Pemetrexed and Cisplatin.

It is particular preferred that Compound (A) is ABTL081 2 and Compound (B) is docetaxel—in particular wherein the cancer is lung cancer (preferably non-small cell lung adenocarcinoma). (See Examples 1.1 and 2.1 herein for an example of this preferred embodiment).

It is particular preferred that Compound (A) is ABTL081 2 and Compound (B) is paclitaxel—in particular wherein the cancer is lung cancer (non-small cell lung cancer). (See Example 1.2 herein for an example of this preferred embodiment).

It is particular preferred that Compound (A) is ABTL081 2 and Compound (B) is gemcitabine—in particular wherein the cancer is pancreatic cancer. (See e.g. Example 1.3 herein for an example of this preferred embodiment).

It is particular preferred that Compound (A) is ABTL081 2 and Compound (B) is carboplatin—in particular wherein the cancer is endometrial cell cancer. (See Example 1.4 herein for an example of this preferred embodiment).

It is particular preferred that Compound (A) is ABTL081 2 and Compound (B) is retinoic acid—in particular wherein the cancer is Neuroblastoma. (See Example 1.5 herein for an example of this preferred embodiment).

It is particular preferred that Compound (A) is ABTL081 2 and Compound (B) is paclitaxel—in particular wherein the cancer is breast cancer (preferably triple negative breast cancer). (See Example 1.6 herein for an example of this preferred embodiment).

It is particular preferred that Compound (A) is ABTL081 2 and Compound (B) is paclitaxel and carboplatin—in particular wherein the cancer is squamous cancer (preferably non-small cell squamous lung cancer). (See Example 2.2 herein for an example of this preferred embodiment).

It is particular preferred that Compound (A) is ABTL081 2 and Compound (B) is paclitaxel and carboplatin—in particular wherein the cancer is non-small cell lung adenocarcinoma. (See Example 2.3 herein for an example of this preferred embodiment).

It is particular preferred that Compound (A) is ABTL081 2 and Compound (B) is pemetrexed and cisplatin—in particular wherein the cancer is non-small cell lung adenocarcinoma. (See Example 2.4 herein for an example of this preferred embodiment).

It is particular preferred that Compound (A) is ABTL081 2 and Compound (B) is paclitaxel—in particular wherein the cancer is endometrial cancer. (See Example 2.5 herein for an example of this preferred embodiment).

It is particular preferred that Compound (A) is ABTL081 2 and Compound (B) is paclitaxel and carboplatin—in particular wherein the cancer is endometrial cancer. (See Example 2.6 herein for an example of this preferred embodiment).

It is particular preferred that Compound (A) is ABTL081 2 and Compound (B) is paclitaxel and Gemcitabine—in particular wherein the cancer is pancreatic cancer. (See Example 2.7 herein for an example of this preferred embodiment).

It is particular preferred that Compound (A) is ABTL081 2 and Compound (B) is either Gemcitabine, or Nab-Paclitaxel and Gemcitabine—in particular wherein the cancer is pancreatic cancer. (See Example 2.8 herein for an example of this preferred embodiment).

It is particular preferred that Compound (A) is ABTL081 2 and Compound (B) is cisplatin—in particular wherein the cancer is neuroblastoma cancer. (See Example 2.9 herein for an example of this preferred embodiment).

It is particular preferred that Compound (A) is ABTL081 2 and Compound (B) is doxorubicin—in particular wherein the cancer is triple negative breast cancer. (See Example 2.10 herein for an example of this preferred embodiment).

It is particular preferred that Compound (A) is ABTL081 2 and Compound (B) is Gemcitabine and Cisplatin—in particular wherein the cancer is cholangiocarcinoma cancer. (See Example 2.11 herein for an example of this preferred embodiment).

It is preferred that Compound (A) is ABTL081 2 and Compound (B) is Temozolomide and Irinotecan—in particular wherein the cancer is neuroblastoma cancer.

It is preferred that Compound (A) is ABTL0812 and Compound (B) is Doxorubicin and Topotecan in particular wherein the cancer is neuroblastoma cancer.

Preferably, the pharmaceutical combination as discussed herein is wherein Compound (A) is ABTL081 2 and wherein:

Compound (B) is docetaxel and the cancer is lung cancer, preferably non-small cell lung adenocarcinoma;
Compound (B) is paclitaxel and the cancer is lung cancer, preferably non-small cell lung adenocarcinoma;
Compound (B) is gemcitabine and the cancer is pancreatic cancer;
Compound (B) is carboplatin and the cancer is endometrial cancer;
Compound (B) is retinoic acid and the cancer is neuroblastoma;
Compound (B) is paclitaxel and the cancer is breast cancer, preferably triple negative breast cancer;
Compound (B) is paclitaxel and carboplatin and the cancer is squamous cell cancer, preferably non-small cell squamous lung cancer;
Compound (B) is paclitaxel and carboplatin and the cancer is non-small cell lung adenocarcinoma;
Compound (B) is pemetrexed and cisplatin and the cancer is non-small cell lung adenocarcinoma;
Compound (B) is paclitaxel and the cancer is endometrial cancer;
Compound (B) is paclitaxel and carboplatin and the cancer is endometrial cancer;
Compound (B) is paclitaxel and gemcitabine and the cancer is pancreatic cancer;
Compound (B) is gemcitabine and the cancer is pancreatic cancer;
Compound (B) is gemcitabine and Nab-paclitaxel and the cancer is pancreatic cancer;
Compound (B) is cisplatin and gemcitabine and the cancer is neuroblastoma;
Compound (B) is doxorubicin acid and the cancer is breast cancer, preferably triple negative breast cancer;
Compound (B) is cisplatin and gemcitabine and the cancer is cholangiocarcinoma;
Compound (B) is gemcitabine and the cancer is cholangiocarcinoma;
Compound (B) is topotecan and the cancer is neuroblastoma;
Compound (B) is irinotecan and the cancer is neuroblastoma; or
Compound (B) is temozolomide and the cancer is neuroblastoma.

As discussed above, Example 4 herein discusses already obtained preliminary results from human critical trials—the already obtained human clinical trials are positive in the sense that these results indicate that there also in human is a synergistic effect in relation to use of the ABTL0812 compound in combination with paclitaxel and carboplatin in patients with advanced endometrial cancer or squamous cell cancer.

Accordingly, it is preferred that the pharmaceutical combination as discussed herein is wherein Compound (A) is ABTL0812 and wherein:

Compound (B) is paclitaxel and carboplatin and the cancer is advanced endometrial cancer, preferably advanced endometrial cancer; or
Compound (B) is paclitaxel and carboplatin and the cancer is squamous cell cancer.

Preferably, ABTL0812 is administered orally-preferably, the administrated dose of ABTL0812 is a dose of from 1200 mg to 1400 mg.

More preferably, ABTL0812 is administered orally, starting at a dose of from 1200 mg to 1400 mg, three times daily in combination with chemotherapy.

A cancer

Preferably, the cancer is at least one cancer selected from the group consisting of:

Lung cancer;
Non-small cell lung cancer;
Small cell lung cancer;
Squamous cell cancer;
Adenocarcinoma;
Endometrial cancer;
Pancreatic cancer;
Glioblastoma;
Breast cancer;
Head and neck cancer;
Neuroblastoma; and
Cholangiocarcinoma.

More preferably, the cancer is at least one cancer selected from the group consisting of:

Non-small cell lung cancer;
Squamous cell cancer;
Endometrial cancer;
Pancreatic cancer;
Glioblastoma;
Breast cancer;
Neuroblastoma; and
Cholangiocarcinoma.

Administration of Compound (A) and/or Compound (B)

As discussed above, in relation to the herein discussed combination treatment is not essential if the two compounds (A) and (B) are administrated e.g. simultaneous as a single composition or e.g. sequentially as two separate compositions. The important matter is that that an effective amount of the compound/agent first administered is in the patient's body when the second compound/agent is administered.

It may be preferred that the pharmaceutical combination as discussed herein is a single composition comprising both Compound (A) and Compound (B).

Compound (A) (in particular ABTL081 2) is preferably administrated orally.

The administrated dose of Compound (A) (in particular ABTL0812) is preferably a dose of from 200 mg to 6000 mg (preferably 2000 mg), more preferably a dose of from 300 mg to 1600 mg and even more preferably a dose of from 450 mg to 1450 mg.

More preferably—the administrated dose of Compound (A) (in particular ABTL081 2) is preferably a total dose of from 200 mg to 6000 mg (preferably 2000 mg) per day, more preferably a total dose of from 300 mg to 1600 mg per day and even more preferably a total dose of from 450 mg to 1450 mg per day. Preferably the total dose is provided by administration from 1 to 5 times a day, more preferably from 2 to 4 times a day and most preferably from 3 times a day.

Accordingly, if the total dose is e.g. 1200 mg per day and it is provided by administration 3 times a day-then may the 3 times e.g. be of 400 mg each.

In relation to Compound (B), a preferred route of administration will generally depend on the chemotherapeutic agent of interest.

Preferred route of administration for preferred Compound (B) is briefly described below:

Docetaxel; —preferably administrated intravenously via infusion solution

Paclitaxel; —preferably administrated intravenously via infusion solution

Carboplatin; —preferably administrated intravenously via infusion solution

Cisplatin; —preferably administrated intravenously via infusion solution

Gemcitabine; —preferably administrated intravenously via infusion solution

Nab-Paclitaxel (Abraxane®); —preferably administrated intravenously via infusion suspension Pemetrexed; —preferably administrated intravenously via infusion solution Doxorubicin; —preferably administrated intravenously Aspects/Embodiments of the Invention in so-Called Claim Format 1. A pharmaceutical combination comprising:
(A): a compound which is a polyunsaturated fatty acid of formula COORi-CHR$_2$—(CH$_2$)a(CH=CHCH2)b-(CH$_2$)c-Cl-13, a pharmaceutically acceptable salt thereof, or a combination thereof, wherein
(i) a can be any integer value between 0 and 7,
(ii) b can be any integer value between 2 and 7,
(iii) c can be any integer value between 0 to 7,
(iv) R$_1$ is H, Na, K, CH$_3$, CH$_3$—CH$_2$, or PO(0-CH$_2$—CH$_3$)$_2$, and
(v) R$_2$ is OH, OCH$_3$, O—CH$_3$COOH, CH$_3$, Cl, CH$_2$OH, OPO(0-CH$_2$—CH$_3$)$_2$, NOH, F, HCOO or N(OCH$_2$CH$_3$)$_2$;
and
(B): a chemotherapeutic agent compound
for the simultaneous, separate or sequential use in the treatment of a cancer in a human patient.

2. The pharmaceutical combination of claim 1, wherein
(i) a can be any integer value between 5 and 7,
(ii) b can be any integer value between 2 and 4, and
(iii) c can be any integer value between 1 to 5.

3. The pharmaceutical combination of any of the preceding claims, wherein R$_1$ is H and R$_2$ is OH.

4. The pharmaceutical combination of any of the preceding claims, wherein Compound (A) is at least one compound or a pharmaceutically acceptable salt thereof selected from the group consisting of:

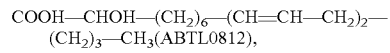

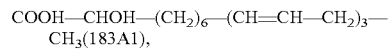

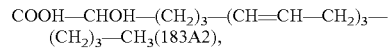

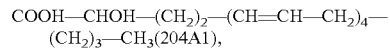

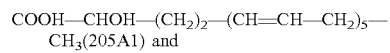

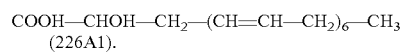

5. The pharmaceutical combination of any of the preceding claims, wherein Compound (A) is COOH—CHOH—(CH$_2$)$_6$—(CH=CH—CH$_2$)$_2$—(CH$_2$)$_3$—CH$_3$ (ABTL081 2) or a pharmaceutically acceptable salt thereof.

6. The pharmaceutical combination of claim 5, wherein Compound (A) is a sodium salt of COOH—CHOH—(CH$_2$)$_6$—(CH=CH—CH$_2$)$_2$—(CH$_2$)$_3$—CH$_3$ (ABTL081 2).

7. The pharmaceutical combination of any of the preceding claims, wherein the cancer is at least one cancer selected from the group consisting of:
Lung cancer;
Non-small cell lung cancer;
Squamous cell cancer;
Adenocarcinoma cancer;
Endometrial cancer;
Serous cancer;
Pancreatic cancer;
Glioblastoma cancer;
Resistant-recurrent breast cancer;
Head and neck cancer;
Neuroblastoma cancer and
Cholangiocarcinoma cancer.

8. The pharmaceutical combination of any of the preceding claims, wherein Compound (B) is at least one chemotherapeutic agent compound selected from the group consisting of:
Docetaxel;
Paclitaxel;
Carboplatin;
Cisplatin;
Gemcitabine;
Nab-Paclitaxel;
Retinoic acid;
Temozolomide;
Irinotecan;
Doxorubicin; and
Topotecan.

9. The pharmaceutical combination of claim 8, wherein Compound (A) is COOH—CHOH—(CH$_2$)$_6$—(CH=CH—CH$_2$)$_2$—(CH$_2$)$_3$—CH$_3$ (ABTL081 2) or a pharmaceutically acceptable salt thereof.

10. The pharmaceutical combination of claim 9, wherein
Compound (B) is docetaxel and the cancer is lung cancer, preferably non-small cell lung adenocarcinoma;
Compound (B) is paclitaxel and the cancer is lung cancer, preferably non-small cell lung adenocarcinoma;

Compound (B) is gemcitabine and the cancer is pancreatic cancer;
Compound (B) is carboplatin and the cancer is endometrial cell cancer;
Compound (B) is retinoic acid and the cancer is Neuroblastoma cancer;
Compound (B) is paclitaxel acid and the cancer is breast cancer, preferably triple negative breast cancer;
Compound (B) is paclitaxel and carboplatin and the cancer is squamous cell cancer, preferably non-small cell squamous lung cancer;
Compound (B) is paclitaxel and carboplatin and the cancer is non-small cell lung adenocarcinoma;
Compound (B) is pemetrexed and cisplatin and the cancer is non-small cell lung adenocarcinoma;
Compound (B) is paclitaxel and the cancer is endometrial cancer;
Compound (B) is paclitaxel and carboplatin and the cancer is endometrial cancer;
Compound (B) is paclitaxel and Gemcitabine and the cancer is pancreatic cancer;
Compound (B) is Gemcitabine and the cancer is pancreatic cancer;
Compound (B) is Gemcitabine and Nab-Paclitaxel and the cancer is pancreatic cancer;
Compound (B) is cisplatin and Gemcitabine and the cancer is neuroblastoma cancer;
Compound (B) is doxorubicin acid and the cancer is breast cancer, preferably triple negative breast cancer; or
Compound (B) is cisplatin and Gemcitabine and the cancer is cholangiocarcinoma cancer.

11. The pharmaceutical combination of any of the preceding claims, wherein the pharmaceutical combination is a single composition comprising both Compound (A) and Compound (B).

12. The pharmaceutical combination of any of the preceding claims, wherein Compound (A) is administrated orally.

13. The pharmaceutical combination of any of the preceding claims, wherein the administrated dose of Compound (A) is a total dose of from 200 mg to 2000 mg per day.

14. The pharmaceutical combination of any of claims 12 to 13, wherein Compound (A) is COOH—CHOH—(CH$_2$)$_6$—(CH=CH—CH$_2$)$_2$—(CH$_2$)$_3$—CH$_3$ (ABTL0812) or a pharmaceutically acceptable salt thereof.

15. The pharmaceutical combination of claim 14, wherein
Compound (B) is Docetaxel and it is administrated intravenously via infusion solution;
Compound (B) is Paclitaxel and it is administrated intravenously via infusion solution;
Compound (B) is Carboplatin and it is administrated intravenously via infusion solution;
Compound (B) is Cisplatin and it is administrated intravenously via infusion solution;
Compound (B) is Gemcitabine and it is administrated intravenously via infusion solution;
Compound (B) is Nab-Paclitaxel and it is administrated intravenously via infusion suspension;
Compound (B) is Temozolomide and it is administrated orally (e.g. in form of capsules);
Compound (B) is Irinotecan and it is administrated intravenously via infusion solution;
Compound (B) is Doxorubicin and it is administrated intravenously; or
Compound (B) is Topotecan and it is administrated intravenously via infusion solution.

EXAMPLES

Example 1: ABTL0812 in Combination with Different Chemotherapeutic Agents—In Vitro Assays 1.1:
Cell viability assays of ABTL0812 in combination with docetaxel in lung cancer
Study reference: ABT-EI
Study site: Protein Kinases & Cell Signaling Group, UAB
GLP compliance: No
Test Compound: ABTL081 2 (batch 006/20 10)
Reference compound: Docetaxel (Fluka, 01855-5 MG-F, batch 1425738V)
Test system: A549 (human lung carcinoma) cell line
Objective: To evaluate the effect of the combination of ABTL081 2 with docetaxel in cell viability. Docetaxel is a cytotoxic compound used in lung cancer; therefore, a potential therapeutic combination in lung cancer may involve the use of ABTL081 2 and docetaxel.

Methods: A549 cells were incubated with increasing concentrations of ABTL081 2 (3-300 μM), docetaxel (0.01-100 μM), or a combination of both (subIC$_{50}$, i.e., 20 μM fixed concentration of ABTL081 2 and 0.01-100 μM docetaxel) for three days (FBS 0.5%). Cell viability was evaluated in all cases by MTT assay and IC$_{50}$'s calculated for ABTL081 2, docetaxel and the combination. Finally, the Combination Index (CI), to evaluate synergism, was calculated according to the method of Chou and Talalay (Chou 2006; Chou 2010), as follows: CI=(D) 1/(Dx)1+(D) 2/(Dx) 2, where CK1, =1, and >1 indicate synergism, additive effect, and antagonism, respectively. In the denominator, (Dx)1 is for D1"alone" that inhibits a system x %, and (Dx)2 is for D2"alone" that inhibits a system x %. In the numerators, (D) 1 and (D) 2"in combination" also inhibit x %. The results shown are the average of two independent experiments.

Results: As expected, ABTL081 2 and docetaxel were cytotoxic when used independently. The addition of a low concentration of ABTL081 2 (20 μM, equivalent to its ICio), dramatically increased docetaxel cytotoxicity. The IC$_5$, for docetaxel in presence of ABTL081 2 was reduced >80 times, i.e. from 1.7 μM to 0.02 μM (see table below and FIG. 1 herein).

| Compound | IC$_{50}$ (μM) |
| --- | --- |
| ABTL081 2 | 42 |
| Docetaxel | 1.7 |
| Docetaxel + 20 μM ABTL081 2 | 0.02 |

Then, the potential synergism of ABTL081 2 with docetaxel was calculated according to the method of Chou and Talalay, (Chou 2006; Chou 2010). The combination of both drug was synergistic in the full range of activities with a CI=0.47 at 50% cell viability. This CI is indicative of synergy.

Conclusions: ABTL081 2 and docetaxel have synergistic effect in vitro in the lung adenocarcinoma cell line A549. A suboptimal concentration of ABTL081 2 (20 μM) reduces more than 80-fold the IC$_{50}$ of docetaxel. These results open the opportunity for the in vivo combination of both drugs in lung cancer. Docetaxel is a drug of choice in several stages of lung cancer; therefore, the combination with ABTL081 2 has a potential beneficial effect, as a synergy between both drugs that increases their cytotoxic effects in lung cancer cells has been observed.

1.2:
Cell Viability Assays of ABTL0812 in Combination with Paclitaxel in Lung Cancer
Study reference: LN3-T30 and ABT-EI-048
Study site: Protein Kinases & Cell Signaling Group, UAB
GLP compliance: No
Test Compound: ABTL081 2 (batch 002/20 12)
Reference compound: Paclitaxel (SelleckChem, S1150-10 MG, batch 09)
Test system: A549 (human lung carcinoma) cell line with mutated KRAS; H157 (human non-small cell lung squamous carcinoma with mutated PTEN; HTB1 82: human non-small cell lung squamous carcinoma and H1975: human non-small cell lung adenocarcinoma with mutated PI3KCA Objective: To evaluate the effect of the combination of ABTL081 2 with paclitaxel, in cell viability. Paclitaxel is a cytotoxic compound used in lung cancer; therefore, a potential therapeutic combination in lung cancer may involve the use of ABTL081 2 and paclitaxel.

Methods: A549 cells were incubated with increasing concentrations of ABTL081 2 (3-300 µM), paclitaxel (0.003-1 µM), or a combination of both using subIC$_{50}$ fixed concentration of ABTL081 2 and 0.003-1 µM paclitaxel for 72 hours in DMEM with 0.1% FBS. H157, H1957 and HTB-81 2 cells were incubated with increasing concentrations of paclitaxel (0.001-10 µM) alone and in combination with subIC50 fixed concentration of ABTL081 2 for 48 hours in DMEM with 0.1% FBS. Cell viability was evaluated in all cases by MTT assay and IC$_{50}$'s were calculated for paclitaxel and the combination. The concentrations of the combinations for the different cell lines were:

A549 cells: ABTL081 2 IC$_{50}$=49 µM. Paclitaxel was combined with 10 (IC10)20 (IC25) and 30 µM (IC35) of ABTL081 2

H157 cells: ABTL081 2 IC$_{50}$=23 µM. Paclitaxel was combined with 10 (IC20) and 15 (IC35) µM of ABTL081 2

H1957 cells: ABTL081 2 IC50=43 µM. Paclitaxel was combined with 10 (IC10) and 20 (IC20) µM of ABTL081 2

HTB-81 2 cells: ABTL081 2 IC$_{50}$=29 µM. Paclitaxel was combined with 10 (IC20) and 15 (IC35) µM of ABTL081 2.

Finally, the Combination Index (CI), as described in the previous section, was calculated for the values of paclitaxel IC$_{50}$.

Results: ABTL081 2 and paclitaxel were cytotoxic in all four lung cancer cell lines. In A549 lung cancer cell line when used independently, the addition of 15, 20 or 30 M of ABTL081 2 increased paclitaxel cytotoxicity. The IC$_{50}$ for the combination was lower than for each drug alone, and a 2 (15 µM and 20 µM) or 7 (30 µM) fold reduction in IC$_{50}$ for paclitaxel was observed. These reductions of paclitaxel IC$_{50}$ were synergistic and CI were 0.34, 0.28 and 0.22 for 15, 20 and 30 UM ABTL0812, respectively. In H157 cells the synergy observed is not as strong as with A549 cells, only potentiating paclitaxel cytotoxicity when combined with 15 UM of ABTL081 2 (IC35), decreasing paclitaxel IC$_{50}$ from 4.19 to 2.39 µM, a 1.75-fold reduction, showing a synergy with a CI of 0.7. In the case of H1957 cells, there is no synergy when ABTL081 2 is added at 10 µM (IC10) and IC$_{50}$ values are not altered (3.68 vs 3.47 µM), but there is a 6.5-fold reduction in IC$_{50}$ value when ABTL081 2 is added at 20 µM (IC20) from 3.68 to 0.56 µM. This reduction of paclitaxel IC$_{50}$ in H1957 was synergistic with a CI of 0.3. Finally, HTB-81 2 cells show good synergy at both concentrations tested, with a 3-fold reduction when ABTL081 2 is added at 10 µM (IC20) from 2.71 to 0.81 µM and a 3.6-fold reduction when ABTL081 2 is added at 20 µM (IC35) from 2.71 to 0.75 µM. These reductions in paclitaxel IC$_{50}$ in HTB-812 cells was synergistic with a CI of 0.4 and 0.5 respectively. See FIG. 2 for further details.

Conclusions: ABTL081 2 and paclitaxel have synergistic effects in vitro in all four lung cancer cell lines tested independently of their mutational status. Suboptimal concentrations of ABTL081 2 reduced the IC$_{50}$ of paclitaxel. These results open the opportunity for the in vivo combination of both drugs in lung cancer.

1.3:
Cell Viability Assay of ABTL081 2 Alone or in Combination with Gemcitabine in Pancreatic Cancer
Study reference: LN1-T56-T58
Study site: Protein Kinases & Cell Signaling Group, UAB
GLP compliance: No
Test Compounds: ABTL081 2 (batch 006/20 10)
Reference compound: Gemcitabine (Sigma, G6423, batch 041 M4727V)
Test system: MiaPaca2 (human pancreatic carcinoma)

Objectives: To study the potential synergism of ABTL081 2 when added to gemcitabine in the pancreatic cancer cell line MiaPaca2. Gemcitabine is considered a standard of care for the treatment of most types of pancreatic cancer. In many cases, mostly for advanced pancreatic cancer it is administered in combination with other drugs (Ghaneh and Neoptolemos 2007); therefore, it is interesting to know whether there is any additive effect between both drugs.

Methods: MiaPaca2 cells were seeded in 24-well plates together with gemcitabine (0.01-100 µM), ABTL081 2 (3-300 µM), or a combination of both (subIC$_{50}$, i.e., 25 µM fixed concentration of ABTL081 2 with 0.01-100 UM gemcitabine) and left in the incubator for 72 h (0.5% FBS). Cell viability was studied by the MTT assay and several parameters were determined to evaluate a possible synergism. First the IC$_{50}$ for each drug alone or the combination was calculated. Then, synergism (CI) was calculated as described above.

Results: The IC$_{50}$ for the combination was lower than for each drug alone, as a 7-fold reduction in IC$_{50}$ for gemcitabine was observed. Note that the ABTL081 2 concentration chosen for the combination experiment had a very low activity alone (<10% cytotoxicity) however it potentiated the cytotoxicity of gemcitabine—see table below and FIG. 3 herein.

| Compound | IC$_{SO}$ (µM) |
| --- | --- |
| ABTL081 2 | 49 |
| Gemcitabine | 10.2 |
| Gemcitabine + 25 µM ABTL081 2 | 1.4 |

The potential synergism of ABTL081 2 with gemcitabine was calculated according to the method of Chou and Talalay (Chou 2006; Chou 2010), for non-constant combination ratios. The combination of both drug was synergistic in the full range of activities with a CI=0.65 at 50% cell viability. This CI is indicative of synergy.

Conclusions: ABTL081 2 and gemcitabine have synergistic effects in vitro in the pancreatic cancer cell line MiaPaca2. A suboptimal concentration of ABTL081 2 (25

M) reduces 7-fold the IC50 of gemcitabine. These results open the opportunity for the in vivo combination of both drugs.

1.4:

Cell Viability Assay of ABTL0812 Alone or in Combination with Carboplatin in Endometrial Cancer Study reference: ABT-EI-065

Study site: Protein Kinases & Cell Signaling Group, UAB

GLP compliance: No

Test Compounds: ABTL081 2 (batch 006/20 10)

Reference compound: Carboplatin (Sigma, C2538)

Test system: Ishikawa (human endometrial carcinoma)

Objectives: To study the potential synergism of ABTL081 2 when added to carboplatin in the endometrial cancer cell line Ishikawa. Carboplatin is considered a standard of care for the treatment of most types of endometrial cancer. Therefore, it is interesting to know whether there is any additive effect between both drugs.

Methods: Ishikawa cells were seeded in 24-well plates together with increasing concentration of carboplatin (1-300 µM) in the presence of 4 µM of ABTL081 2 (equivalent to an IC10) for 48 h (0.5% FBS). Cell viability was studied by the MTT assay and several parameters were determined to evaluate a possible synergism. First the $IC_{50}$ for each drug alone or the combination was calculated.

Results: The $IC_{50}$ for the combination was lower than for each drug alone, as a 3-fold reduction in $IC_{50}$ for carboplatin was observed. Note that the ABTL081 2 concentration chosen for the combination experiment had a very low activity alone (<10% cytotoxicity) however it potentiated the cytotoxicity of gemcitabine-see FIG. 4 herein.

Conclusions: ABTL081 2 and carboplatin have synergistic effects in vitro in the endometrial cancer cell line Ishikawa. A suboptimal concentration of ABTL081 2 (4 µM) reduces 3-fold the IC50 of carboplatin. These results open the opportunity for the in vivo combination of both drugs.

1.5:

Cell viability assay of ABTL0812 alone or in combination with retinoic acid in neuroblastoma Study reference: ABT-EI-055

Study site: Laboratory of Translational Research in Pediatric Cancer (VHIR)

GLP compliance: No

Test Compounds: ABTL081 2 (batch 006/20 10)

Reference compound: retinoic acid (Sigma, R2625)

Test system: SK-N-BE (2): human neuroblastoma cell line and LA1-5S: clonal subline of the neuroblastoma cell line LA-N-1

Objectives: To evaluate the effect of the combination of ABTL081 2 with retinoic acid (RA) on cell viability in the neuroblastoma cell lines SK-N-BE (2) and LA1-5S.

Methods: LA1-5S and SK-N-BE (2) cells were incubated with a $subIC_{50}$ fixed concentration of ABTL0812 (30 µM), increasing concentrations of 10 µM, 20 µM and 30 µM of retinoic acid or a combination of both. 10 µM retinoic acid is the pharmacological dosage administered orally in phase I trials to neuroblastoma patients (Villablanca et al. 1995). Cells were treated for 24 h in IMDM with 0.5% FBS. Cell viability was evaluated in all cases by crystal violet assay. Different doses were assessed in six replicates and the results shown are the average of two independent experiments. Statistical analyses were performed according to the T-Test principle with GraphPad Prism® 5.0 software (* p<0.05;  p<0.01; * p<0.001).

Results: ABTL0812 showed a mild cytotoxicity in both LA1-5S and SK-N-BE (2) neuroblastoma cell lines when used as single agent at low concentrations; retinoic acid efficacy at concentrations 10 µM and 20 µM was even lower. The combination of 30 UM ABTL081 2 and retinoic acid resulted in high cytotoxicity in both neuroblastoma cell lines. The percentage of dead/non-proliferating cells was higher than for each drug alone in any of the combinations, which suggests a synergistic effect. The increase in cell death was statistically significant at all concentrations (*** p<0.001). For further details see FIG. 5 herein.

Conclusions: The combination of ABTL0812 and RA has a strong synergetic effect, that potentiates their cytotoxic activity in vitro in the neuroblastoma cell lines SK-N-BE (2) and LA1-5S. RA is commonly used in clinics for the management of neuroblastoma minimal residual disease phase, therefore, this data encourages the further investigation of this combination to manage neuroblastoma.

1.6:

Cell Viability Assay of ABTL0812 Alone or in Combination with Paclitaxel in Breast Cancer Study reference: pending Study site: Targets lab, UdG GLP compliance: No Test Compounds: ABTL081 2 (batch 006/2010)

Reference compound: Paclitaxel (SelleckChem, S1150)

Test system: MDB-DA-23 1 (human triple negative breast cancer)

Objectives: To study the potential synergism of ABTL0812 when added to paclitaxel in the triple negative breast cancer cell line MDB-DA-231.

Methods: MDB-DA-231 cells were seeded in 24-well plates together with increasing concentration of paclitaxel (1-100 nM) in the presence of 5, 10 and 20 µM of ABTL081 2 (all doses below to an IC25) for 48 h (0.5% FBS). Cell viability was studied by the MTT assay and several parameters were determined to evaluate a possible synergism. First the $IC_{50}$ for each drug alone or the combination was calculated.

Results: The $IC_{50}$ for the combination was lower than for each drug alone, as a 2.7-fold reduction in $IC_{50}$ for paclitaxel was observed. Note that the ABTL081 2 concentration chosen for the combination experiment had a very low activity alone (<10% cytotoxicity) however it potentiated the cytotoxicity of paclitaxel, showing a strong synergy with CI values of 0.3, 0.2 and 0.16 for 5, 10 and 20 µM of ABTL081 2 respectively-see table below and FIG. 6 herein.

| Compound | $IC_{50}$ |
| --- | --- |
| ABTL0812 | 29 µM |
| Paclitaxel | 8.7 nM |
| Paclitaxel + 5 µM ABTL0812 | 5.1 nM |
| Paclitaxel + 10 µM ABTL0812 | 3.2 nM |
| Paclitaxel + 20 µM ABTL0812 | 3.2 nM |

Conclusions: ABTL081 2 and carboplatin have synergistic effects in vitro in the endometrial cancer cell line Ishikawa. A suboptimal concentration of ABTL081 2 (4 µM) reduces 3-fold the IC50 of carboplatin. These results open the opportunity for the in vivo combination of both drugs.

Example 2: ABTL0812 in Combination with Different Chemotherapeutic Agents—In Vivo Assays 2.1:
A549 Xenograft in Mice in Combination with Docetaxel
  Study reference: ALM-IDIBAPS
  Study site: Molecular and Translational Oncology Research Group. IDIBAPS, Hospital Clinic Barcelona.
  GLP compliance: No
  Test compound: ABTL081 2 (batch 002/20 12)
  Reference compound: Docetaxel.
  Test System: Nu/nu male mice
  Objective: Investigate the anti-tumor activity of ABTL081 2 alone and in combination with docetaxel, a reference drug for the treatment of NSCLC.
  Methods: Mice were injected with $5\times10^6$ A549 cells in each flank to induce tumor formation. 20 days later, when tumors had a volume of 50 mm 3 approximately, animals were homogenously randomized and the different treatments were started. ABTL081 2 was administered by the oral route at 30 mg/kg/day, 5 times a week. Docetaxel 5 mg/kg was administered intra-peritoneally once a week (Coxon et al. 2012). Tumor volume and body weight were monitorized 3 times a week.
  Results: ABTL081 2 significantly reduced tumor volume when compared to control animals (ANOVA followed by t-test). ABTL081 2 efficacy was indeed similarly to the efficacy observed for docetaxel treatment. Interestingly, ABTL081 2 potentiated the antitumor effect of docetaxel. Statistical analysis showed that this combination therapy significantly improves the reduction of tumor growth compared to docetaxel alone (p<0.001 by t-test). In addition, no decrease in body weight or hematological counts (not shown) were observed in any of the treatment groups, including those where ABTL081 2 is administered with docetaxel, suggesting this combination had no toxic effects. In relation to the anti-tumor effect of the combination of ABTL081 2 and Docetaxel in the A549 lung cancer xenograft models, all the treatments significantly reduced tumor volume vs. control at sacrifice (*, ANOVA followed by t-test analysis). In addition, the combination 30 mg/kg ABTL081 2+docetaxel was significantly more efficacious than the treatment with docetaxel alone (** p<0.01, t-test). On the other hand, no impact on body weigh was observed with any of the treatments either alone or their combination. For further details see FIG. 7 herein.
  Conclusion: ABTL081 2 reduces tumor growth in xenograft models of lung cancer derived from A549 cells. In this model, ABTL081 2 has an efficacy that is similar to the SOC docetaxel. ABTL081 2 and docetaxel as single therapy similarly reduced tumor volume in a xenograft model of lung cancer derived from A549 cells. ABTL081 2 potentiate the antitumor activity of Docetaxel with no toxic effect. These results suggest a combined therapy of ABTL081 2 plus Docetaxel could have a clinical interest for the treatment of lung cancer.

2.2:
Efficacy of ABTL081 2 in Combination with Paclitaxel and Carboplatin in a Human Squamous NSCLC (H157) Xenograft in Mice
  Study reference: ALM-IDIBAPS
  Study site: Molecular and Translational Oncology Research Group. IDIBAPS, Hospital Clinic Barcelona.
  GLP compliance: No
  Test compound: ABTL081 2 (batch K102E)
  Test System: Nu/nu male mice
  Objective: Investigate survival rate for ABTL081 2 alone and in combination with paclitaxel and carboplatin (P/C) with a Kaplan-Meier analysis in a human squamous NSCLC xenograft model
  Methods: Mice were injected with $5\times10^6$ H157 cells in one flank to induce tumor formation. When tumors had a volume of 100 mm$^3$ approximately, animals were homogenously randomized (n=8 per group) and the different treatments were started. The different conditions studied were vehicle, 120 mg/kg oral ABTL081 2 daily, 15 mg/kg carboplatin+50 mg/kg paclitaxel by i.p. route and an additional group receiving the combination of these two regimens. ABTL081 2 was administered always two days prior to the first P/C administration and two days after, maintaining 4 doses of ABTL081 2 and one of P/C per week. Tumor volume was monitored 3 times a week. To perform Kaplan-Meier plot, the end-point criteria to exclude animals from the study was a tumor volume superior to >1000 mm$^3$ or different indicators of animal welfare validated by an Ethics Committee. Different groups were maintained under treatment until all animals from each group reached 1000 mm$^3$ or welfare-related endpoint criteria, except for the group ABTL081 2+P/C, where mice had to be sacrificed before they reach 1000 mm$^3$ to end experimental procedure.
  Results: ABTL081 2 treatment in combination with P/C shows the most effective therapy in a Kaplan-Meier analysis. As seen in the FIG. 8 herein, the combination of ABTL081 2+P/C is the most effective treatment in terms of survival rate, showing a significant benefit over the other groups. At day 20 after the beginning of the treatments, ABTL081 2+P/C treatment shows a 75% of survival, compared with 0% for ABTL081 2 and P/C groups and 20% for vehicle group, without showing any relevant signs of toxicity.
  Conclusion: Endpoint criteria was set up based on different measurements of animal welfare indicators and indicative of endpoint decision. When animal health status was stable, 1000 mm$^3$ of tumor volume was set as the endpoint criteria. Under these conditions, the combination of ABTL081 2+P/C treatment shows significant increase in the survival rate measured by Kaplan-Meier analysis in a H157-squamous NSCLC xenograft model, with a 75% of survival at 20 days after treatments and comparted with 0% survival in ABTL081 2 and vehicle and 25% survival in P/C group.

2.3: Efficacy of ABTL0812 in Combination with Paclitaxel and Carboplatin in a Human Adenocarcinoma NSCLC (H1975) Xenograft in Mice
  Study reference: ABT-EI-049
  Study site: Molecular and Translational Oncology Research Group. IDIBAPS, Hospital Clinic Barcelona.
  GLP compliance: No
  Test compound: ABTL081 2 (batch 002/20 12)
  Reference compounds: paclitaxel (Selleckchem #S1150) carboplatin (Sigma Aldrich #C2538)
  Test System: Nu/nu male mice
  Objective: Investigate the anti-tumor activity of ABTL0812 alone and in combination with paclitaxel and carboplatin in a human lung adenocarcinoma xenograft. Paclitaxel and carboplatin combo is one of one of the reference therapies for the treatment of NSCLC.
  Methods: H1975 cell line was routinely cultured in DMEM 10% FBS and cells in an exponential growth phase were harvested and counted for tumor inoculation. Mice were injected in one flank with 2.5×106 H1957 cells suspended in 50 µl of growth medium without FBS and 50 µl of Matrigel (Corning #354234). Tumor volume was monitored 3 days a week and when tumors reached 100 mm$^3$ (between 50 and 150 mm$^3$), animals were homogeneously distributed into four treatment groups showing a similar average intragroup tumor volume, excluding tumors smaller than 50 mm$^3$ or greater than 150 mm$^3$ to minimize variabilities.

Treatment groups were:
  Vehicle group (n=7): treated orally with 200 µl of water+ 5% glycerol four days a week and two injections i.p. of 100 prof saline solution once a week
  ABTL081 2 (n=9): treated orally with 200 µl of 120 mg/kg of ABTL081 2 resuspended in water+5% glycerol 5 times a week
  Paclitaxel/carboplatin (n=9): treated with 100 µl of 15 mg/kg of paclitaxel administered i.p. and 100 µl of 5 mg/kg of carboplatin administered i.p. once a week
  ABTL0812+paclitaxel/carboplatin (n=9): treated orally with 200 µl of 120 mg/kg of ABTL081 2 four days a week and 100 µl of 15 mg/kg of paclitaxel administered i.p. and 100 µl of 5 mg/kg of carboplatin administered i.p. once a week Results: ABTL081 2 administered in combination with paclitaxel and carboplatin shows the best anti-tumor effect in vivo in xenografts derived from H1957 cells. While administration of paclitaxel and carboplatin reduced tumor volume compared with vehicle group, ABTL0812 administered alone showed a similar tumor volume reduction with an improved tendency, the triple combination ABTL0812+paclitaxel and carboplatin showed the highest tumor volume reduction, with significant difference. In addition, a slight decrease in body weight was observed during the first week of treatment on the triple combination group, that gets stabilized for the rest of the experiment. (no decrease in body weight or hematological counts (not shown) were observed in any of the treatment groups, including those where ABTL0812 is administered with docetaxel, suggesting this combination had no toxic effects. For further details see FIG. 9 herein.

Conclusion: ABTL081 2 administered orally reduces tumor growth in xenograft models of lung cancer derived from H1975 cells. In this model, ABTL0812 has an efficacy that is similar to the SOC paclitaxel+carboplatin. Additionally, ABTL0812 potentiates the antitumor activity of Paclitaxel/Carboplatin with no toxic effect. These results suggest a combined therapy of ABTL081 2 plus Paclitaxel/Carboplatin could have a clinical interest for the treatment of lung cancer.

2.4: Efficacy of ABTL0812 in Combination with Pemetrexed and Cisplatin in a Human Adenocarcinoma NSCLC (A549) Xenograft in Mice
  Study reference: ABT-EI-052
  Study site: Protein Kinases & Cell Signaling Group, UAB
  GLP compliance: No
  Test compound: ABTL081 2 (batch K 102E)
  Reference compound: Pemetrexed (Sigma Aldrich #PHR1596) and Cisplatin (Sigma Aldrich #P4394)
  Test System: Nu/nu male mice
  Objective: The aim of this study was to evaluate the anti-tumor efficacy of ABTL081 2 alone or in combination with standard of care chemotherapy pemetrexed and cisplatin for treating subcutaneous xenograft model of lung cancer in immunosuppressed nude mice implanted with human lung adenocarcinoma A549 cells.
  Methods: A549 cell line was routinely cultured in DMEM 10% FBS and cells in an exponential growth phase were harvested and counted for tumor inoculation. 50 female 8 weeks old nude mice were injected in one flank with 5×106 MiaPaca2 cells suspended in 50 µl of growth medium without FBS and 50 µl of Matrigel (Corning #354234). Tumor volume was monitored 3 days a week and when tumors reached 100 mm$^3$ (between 50 and 150 mm$^3$), animals were homogeneously distributed into three treatment groups showing a similar average intragroup tumor volume, excluding tumors smaller than 50 mm$^3$ or greater than 150 mm$^3$ to minimize variability. Treatment groups were:
  Vehicle group (n=7): treated orally with 200 µl of water+ 5% glycerol 4 times a week and i.p. twice a week with 200 µl of saline buffer (chemotherapy vehicle)
  Pemetrexed/Cisplatin (n=20): treated i.p. twice a week with 100 µl of 100 mg/kg pemetrexed and i.p. once a week with 100 µl of 2 mg/kg of cisplatin
  ABTL081 2+pemetrexed/cisplatin (n=20): treated orally with 200 µl of 120 mg/kg of ABTL081 2 resuspended in water+5% glycerol 4 times a week and i.p. with 100 µl of 100 mg/kg pemetrexed and i.p. once a week with 100 µl of 2 mg/kg of cisplatin Results: As seen in FIG. 1, ABTL081 2 administered in combination with pemetrexed and cisplatin shows a strong anti-tumor effect with potentiation of pemetrexed/cisplatin therapeutic effect, thus allowing for a significant reduction in tumor volume compared with pemetrexed/cisplatin treatment group. ABTL081 2+pemetrexed/cisplatin showed a significant tumor reduction compared to pemetrexed/cisplatin from day 33 of treatment, difference that was more significative in following days until the last day of treatment on day 41. Both treatment groups, pemetrexed/cisplatin and ABTL081 2+pemetrexed/cisplatin showed significant tumor volume reduction compare with vehicle group from day 22 of treatment until the last day of treatment on day 41.

In terms of toxicity derived from treatments, FIG. 2 shows the time-course of total body weight for all four groups that was monitored over the 41 days of treatment. Although no signs of toxicity or clinicopathological symptoms were seen, a slight decrease during the first week of treatment in the ABTL081 2+pemetrexed/cisplatin group compared with the rest was observed, due to decrease in food intake in days where chemotherapy was administered. No additional clinical pathological signs were observed in any of the groups. For further details see FIG. 10 herein.

Conclusion: As described earlier, ABTL081 2 reduces tumor growth in xenograft models of lung cancer derived from A549 cells. In this model, ABTL081 2 potentiates the antitumor activity of pemetrexed and cisplatin with no toxic effect. Pemetrexed and cisplatin therapy is the most common first line treatment option for lung adenocarcinoma cancer patients, thus these results suggests that a combined therapy of ABTL081 2 plus pemetrexed and cisplatin could have a clinical interest for the treatment of lung cancer patients.

2.5:
Efficacy Study of ABTL0812 Combined with Paclitaxel in an Endometrial Orthotopic Model in Mice
  Study site: Xenopat (Barcelona, Spain)
  GLP Study: No
  Test compounds: ABTL081 2 (batch 001R/2014), paclitaxel (Teva)
  Test system: Athymic Nude-Foxn1 nu female mice
  Objective: To evaluate the antitumor efficacy of orally administered ABTL081 2 combined with ip paclitaxel in Ishikawa orthotopic model of endometrial cancer.
  Methods: Female mice were orthotopically implanted in the uterus with a 3 mm$^3$ piece of Ishikawa cell line derived tumor. Before starting drug treatment, all animals were weighted and tumor volumes were assessed by palpation. Mice were assigned into groups using randomized block design based upon their tumor volumes. Paclitaxel was i.p. administered every 7 days (15 mg/kg). ABTL081 2 was administered by oral gavage and its administration schedule is 5 days on 2 days off (120 mg/kg/day). Overall, the animals were divided in four administration groups as shown in the Table below.

TABLE

Administration groups in the endometrium cancer orthotopic model.

| Treatment | Dose (mg/kg) | n | Dosing Route | Planned Schedule |
|---|---|---|---|---|
| Vehicle | — | 7 | o.g. | QD 5 days on/2 days off |
| Paclitaxel | 15 | 9 | i.p. | Every 7 days |
| ABTL | 120 | 10 | o.g. | QD 5 days on/2 days off |
| Paclitaxel/ ABTL081 2 | 15/120 | 10 | i.p./o.g. | Every 7 days QD 5 days on/2 days off |

Tumor volume was estimated according to the formula $V=\pi/6 \times L \times W^2$, where L is the long axis and W is the short axis of tumor, respectively. At the time of routine monitoring, animals were checked for effects of tumor growth and treatments on normal behavior such as mobility, visual estimation of food, body weight gain/loss (body weights were measured twice weekly during drug administration), eye/hair matting and any other abnormal effect. Death and observed clinical signs were recorded based on the number of animal within each subset.

Given that orthotopic tumors can only be measured at sacrifice, a set of animals (n=2-3 per group) was sacrificed after one week of treatment to determine early effects on tumor growth. Most of the animals were sacrificed after 3 weeks of treatment (n=5-7 per group).

Results: A set of mice (n=36) were orthotopically implanted with a 3 mm³ Ishikawa cell line derived tumor fragment. No effects on animal behavior were recorded during the whole experimental treatment. Animals treated with the combination paclitaxel showed a reduced tumor weight gain, and some weight loss that was partially recovered at the end of the treatment period. Given that this weight loss compared with control group did not reach 10%, it was not considered to be toxic. Animals were sacrificed after drug treatment was administered for one or three weeks and tumor volume determined as indicated in methods. No differences were observed in those animals that were treated for one week. However, in those animals that were treated for three weeks an additive effect was observed for those animals treated with the combination paclitaxel+ABTL081 2—see FIG. 11 herein.

Conclusions: The combination ABTL081 2+paclitaxel has shown a synergistic effect vs. the effect of each drug alone, as a significant tumor volume reduction was observed in animals treated with the combination vs. control animals. At the same time, some body weight reduction was observed in animals treated with the combination. However, this effect was not regarded to be toxic.

2.6:
Efficacy Study of ABTL0812 Combined with Paclitaxel and Carboplatin in a Patient-Derived Xenograft (PDX) Endometrial Model in Mice Study reference: ABT-EI-043
Study site: VHIR
GLP compliance: No
Test compound: ABTL081 2 (batch K 102E=MEI-014-15)
Reference compounds: paclitaxel (Selleckchem #S1150) carboplatin (Sigma Aldrich #C2538)
Test System: Athymic Nude-Foxn1 nu female mice
Objective: Investigate the anti-tumor activity of ABTL0812 alone and in combination with paclitaxel and carboplatin (P/C) in a PDX model subcutaneously implanted in nude mice.

Methods: A tumor surgically removed from a patient with serous histology, grade IIIC2, 100% of myometrial invasion and pelvis and aortic lymph node and lymph vascular space invasion and carrying mutations in p53 and PI3KCA gene was implanted in one flank of several nude mice. After tumors grew up to 100 mm³, tumors were extracted from mice, minced in 2 mm long pieces and re-implanted in one flank of 40 mice. When average tumor volume reached 100 mm³, mice were randomly distributed into treatment groups, and dosed as follows: vehicle (n=11); ABTL081 2:120 mg/kg orally, 5 times per week (n=10); paclitaxel/carboplatin (P/C): P: 50 mg/kg/C: 15 mg/kg intraperitoneal (n=12); and ABTL081 2+P/C: ABTL081 2 (n=10) was administered always two days prior to the first P/C administration and two days after, maintaining 4 doses of ABTL081 2 and one of P/C per week; doses were the same as when given separately.

The effectiveness of the therapy was measured by the impact of the treatment on the tumor growth, which was measured by its volume. The health state of the animals and the drug-induced toxicity were determined by the animal body weight during the study. Tumor size evolution and tumor weight were evaluated by two-way ANOVA (day by day analysis).

In order to simulate the Phase II clinical trial design, where ABTL081 2 will be administered chronically after P/C cycles, P/C treatment was removed from P/C and ABTL081 2+P/C groups, maintaining ABTL081 2 chronically. Tumor volume was measure after P/C treatment removal during an extra 17 days.

Results: A set of 40 mice were randomly distributed in four groups of treatment when tumors reached around 100 mm³. As shown in FIG. 12 herein, 47 days after treatment began, ABTL0812+P/C showed the highest efficacy and statistically significant tumor growth reduction compared with vehicle, ABTL0812 alone and P/C alone. The improved therapeutic outcome was not associated to increased signs of toxicity, as seen by the absence of significant weight loss in total body weight. ABTL081 2 administered alone shows same efficacy as P/C without any signs of relevant toxicity.

At day 47, P/C administration was stopped while maintaining ABTL081 2 chronically 5 days a week to determine if maintained administration of ABTL0812 can avoid or delay tumor relapse. While P/C group, where mice stopped receiving treatment, tumor continued to grow with similar o slightly higher slope, ABTL0812+P/C group that maintained ABTL081 2 administration, not only did not show increase in tumor growth ratio, but also showed signs of remission. ABTL081 2 group, which maintained ABTL081 2 during the whole experiment, showed a tumor growth inhibition very similar to P/C, maintaining a constant growth slope, indicative of no signs of resistance process that would have increased the growth ratio.

Conclusion: The combination ABTL081 2+P/C has shown a synergistic effect, showing a significant higher tumor volume reduction compared to P/C alone, which also shows a significant tumor volume reduction compared to vehicle group during the first 47 days. ABTL081 2 administered as a monotherapy shows the same efficacy reducing tumor growth as that obtained by the administration of P/C. Body weight reduction was observed partially only in ABTL081 2 group at day 15, recovering that reduction in weight in the next four days and maintained stable for the rest of the experiment. None of the other groups showed any effect regarded to be toxic.

In an attempt to simulate Phase II clinical trial in humans, where ABTL081 2 will be administered in combination with P/C as a first line and ABTL081 2 will remain chronically after the chemotherapy cycles, we removed P/C treatment at day 47 while maintaining ABTL081 2. While tumor growth from P/C and ABL081 2 was not reduced, chronic administration of ABTL081 2 is efficacious avoiding tumor relapse after P/C treatment in this human endometrial PDX, showing signs of remission 10 days after chemotherapy removal.

2.7:
Efficacy Study of ABTL0812 Administered in Combination with Paclitaxel/Gemcitabine (P/Gm) in a Human Pancreatic Xenograft Model in Mice Implanted with MiaPaca-2 Cells
  Study reference: ABT_EI_001_XP
  Study site: Ability Virtual Lab-UAB
  GLP compliance: No
  Test compound: ABTL081 2 (batch K 102E=MEI-014-15)
  Reference compound: Paclitaxel/Gemcitabine (P/Gm)
  Test System: Athymic Nude-Foxn1 nu female mice
  Objective: To evaluate the antitumor efficacy of ABTL0812 by the oral route in combination with P/Gm in a MiaPaCa2 xenograft mouse model of pancreatic cancer. P/Gm administered i.p. was used as positive control, along with vehicle, ABTL081 2 and the combination of ABTL081 2+P/Gm. Efficacy was assessed by tumor growth, and tolerability of the compound and toxicity by the evolution of animal weight.

Methods: Athymic female nude mice (n=9 per group) were injected via subcutaneous route with 0.1 ml of MiaPaca2 cells ($5\times10^6$ cell/ml in serum free DMEM media in 1:1 with matrigel) in one flank. Tumor Volumes (TV) were measured as length×width$^2$×½ three times a week. When average tumor volume reached 100 mm$^3$, mice were randomly distributed into treatment groups and dosed as follows: vehicle; ABTL081 2 120 mg/kg, 5 times per week; P/Gm 15 mg/kg and 60 mg/kg two times per week and the combination of ABTL081 2+P/Gm, where ABTL081 2 was given four times a week (days 1, 2 4 and 5), always two days prior to the administration of P/Gm (days 3 and 6) for a total of 4 weeks.

The effectiveness of the therapy was measured by the impact of the treatment on the tumor growth, which was measured by its volume. The health state of the animals and the drug-induced toxicity were determined by the animal body weight during the study. Tumor size evolution was evaluated by two-way ANOVA (day by day analysis) and by Student t-test in days with significant differences were found.

Results: The graphs of FIG. 13 herein show the effect of ABTL081 2 administered orally in combination with P/Gm on relative tumor volume and total body weight as a measure of toxicity. ABTL081 2 in combination with P/Gm shows the highest efficacy, significantly reducing tumor volume compared with P/Gm alone at the indicated times. Additionally, ABTL081 2+P/Gm combination treatment shows tumor regression in all animals from day 10 after treatment, contrary to that observed with the rest of the groups. ABTL081 2 alone seems to have a positive effect within the first 15 days after treatment, showing similar tumor volume to vehicle group in the following days. P/Gm treatment at the indicated doses reduces tumor volume compared with vehicle and ABTL081 2 groups, but without statistical significance at any time analyzed. In the total body weight graphic, we can see the impact of the combination of ABTL081 2+P/Gm in total body weight compared to the rest of the groups. Although there is a slight loose of weight after the first doses of ABTL081 2+P/Gm, toxicity derived from the combination was minimum and acute toxic effects were not present in any of the animals during the experiment.

Conclusion: The combination ABTL081 2+P/Gm has shown a synergistic effect with a significant higher tumor volume reduction compared to P/Gm alone. P/Gm also shows a higher tumor volume reduction compared to vehicle and ABTL081 2 groups, although not statistically significant. ABTL081 2 administered as a monotherapy shows the same tumor growth curve that that obtained with the vehicle group. Is noteworthy to point out that ABTL081 2+P/Gm treatment can induce tumor regression in all individual animals treated with the combination, maintaining tumor volume around 100 mm$^3$ until day 10 of treatment and below 100 mm$^3$ after day 10 of treatment, indicative of tumor regression. Body weight reduction was observed partially in ABTL081 2+P/Gm group, although none of the mice from any group showed any effect regarded to be toxic.

2.8:
Efficacy Study of ABTL0812 Administered in Combination with Nab-Paclitaxel/Gemcitabine (NabPac/Gm) in a Human Pancreatic Xenograft Model in Mice Implanted with MiaPaca-2 Cells
  Study reference: ABT-EI-053
  Study site: Ability Virtual Lab-UAB
  GLP compliance: No
  Test compound: ABTL081 2 (batch K 102E=MEI-014-15)
  Reference compound: Gemcitabine-Hydrochloride (Sigma Aldrich G6423). Nab-Paclitaxel (Abraxane; ID: 3369272 Celgene)
  Test System: Athymic Nude-Foxn1 nu female mice
  Objective: The objective of this study was to evaluate the efficacy and safety of ABTL0812 administered orally to potentiate the anti-tumor effects of Standard of Care (SOC) chemotherapy gemcitabine and combo gemcitabine/Nab-Paclitaxel administered intraperitoneally (i.p.), in an in vivo human pancreatic xenograft model in immunosuppressed nude mice implanted with MiaPaca2 cells. Both chemotherapy options are the most common first line therapy for treating advanced pancreatic cancer in humans.

Methods: MiaPaca2 cell line was routinely cultured and cells in an exponential growth phase were harvested and counted for tumor inoculation. 55 immunodeficient athymic nude female mice were subcutaneously injected with 5×106 MiaPaca2 cells suspended in 50 µl of growth medium without FBS and 50 µl of Matrigel (Corning #354234) in the one flank. Tumor volume was monitored 3 days a week and when tumors reached 100 mm$^3$ (between 50 and 150 mm$^3$), animals were homogeneously distributed into six treatment groups showing a similar average intragroup tumor volume and excluding tumors smaller than 50 mm³ or greater than 150 mm³ to minimize variability.

Treatment groups were:
Vehicle group (n=9): treated orally with 200 μl of water+ 5% glycerol 5 times a week (ABTL081 2 vehicle) and i.p. twice a week with 200 μl of saline buffer (chemotherapy vehicle).
ABTL081 2 (n=9): treated orally with 120 mg/kg in 200 μl of distilled water+5% glycerol, 5 times a week.
Gemcitabine (n=9): treated i.p. with 60 mg/kg in 100 μl of sterile water, 2 times a week.
Gemcitabine+Nab-Paclitaxel (n=8): Nab-Paclitaxel was freshly prepared from a powder stock (10% (m/m) in 0.9% NaCl solution and was administered i.p. at 5 mg/kg in 230 μl, 2 times a week. Gemcitabine was administered i.p. at 60 mg/kg in 100 μl of sterile water, 2 times a week. It is important to change the site of injection to avoid intestinal necrosis and keep Nab-Paclitaxel and gemcitabine injections as far as possible one from the other in mice abdomen.
Gemcitabine+ABTL081 2 (n=10): treated orally with 120 mg/kg of ABTL081 2 in 200 μl of distilled water+5% glycerol, 5 times a week and with 60 mg/kg of gemcitabine administered i.p in 100 μl of sterile water, 2 times a week. ABTL081 2 was always administered before chemotherapy with the aim of reducing the stress derived from the i.p. injection, that is normally applied as the last administration.
Gemcitabine+Nab-Paclitaxel+ABTL0812 (n=8): treated orally with 120 mg/kg of ABTL081 2 in 200 μl of distilled water+5% glycerol, 5 times a week, with 60 mg/kg of gemcitabine administered i.p. in 100 μl of sterile water, 2 times a week and with 5 mg/kg of Nab-Paclitaxel administered i.p. in 230 μl of 0.9% NaCl solution 2 times a week. As in the gemcitabine+ Nab-Paclitaxel group, injections where administered in separated areas of the abdomen. ABTL0812 was always administered before chemotherapy with the aim of reducing the stress derived from the i.p. injection.

Treatment efficacy was assessed by measuring tumor volume three days a week. Additionally, total body weight was monitored three days a week to test the toxicity associated with the treatments in addition to visual examination of signs indicative of clinicopathological symptoms. At the end of the study, mice were euthanized by carbon dioxide inhalation and death was further confirmed by cervical dislocation.

Results: We selected a suboptimal dose of chemotherapy (based on bibliography) with the aim of not having a strong anti-tumor response that could be potentiated by ABTL081 2, thus allowing for a reduction of the chemotherapy dose and consequently decrease its unwanted adverse events. FIG. 14 shows the tumor volume progression of a MiaPaca2-derived xenograft treated with different regimes of chemotherapy, ABTL081 2 or the combination of both. FIG. 14A shows the tumor volume progression of gemcitabine+Nab-Pac treated xenografts compared with gemcitabine+Nab-Pac+ABTL081 2 treatment, in addition to ABTL081 2 and vehicle treatments. When compared to vehicle group, only the triple combination Gem+Nab-Pac+ ABTL081 2 shows a significant tumor volume reduction, starting from day 22 and maintaining this statistical significance until the end of the study, with the last five days of treatment showing the highest tumor volume difference and in contrast with Gem+Nab-Pac group, that do not show significant difference in tumor volume compared with vehicle group. When comparing Gem+Nab-Pac+ABTL081 2 vs Gem+Nab-Pac, the triple combination significantly reduces tumor volume at the last day of the treatments. It can also be observed, that ABTL081 2 administered alone shows a better response in tumor volume evolution than Gem+ Nab-Pac group during the first 20 days of treatment, getting similar tumor volume evolution for the rest of the study, although no significant differences were observed at any time point.

FIG. 14B shows the tumor volume progression of gemcitabine treated xenografts compared with gemcitabine+ ABTL081 2 treatment, in addition to ABTL081 2 and vehicle treatments. When compared to vehicle group, only the double combination Gem+ABTL081 2 shows a significant tumor volume reduction, starting from day 17 and maintaining this statistical significance until the end of the study, in contrast with gemcitabine group, that do not show significant difference in tumor volume compared with vehicle group. When comparing Gem vs Gem+ABTL081 2, the double combination significantly reduces tumor volume at the last day of the treatments. It can also be observed that ABTL081 2 administered alone shows a better response in tumor volume evolution than Gem group during the whole study, although no significant differences were observed at any time point.

Mice total body weight was monitored three times a week during the whole study FIG. 14C shows total body weight evolution for Gem+Nab-Pac and Gem+Nab-Pa+ABTL081 2 in addition to vehicle and ABTL081 2 groups, and FIG. 14D shows total body weight evolution for Gem and Gem+ ABTL081 2 in addition to vehicle and ABTL081 2 groups. No signs of toxicity were observed in any of the groups in terms of body weight loss, with all the groups showing gain of weight during the whole study, indicative of lack of toxicity associated to the treatments. No additional clinical pathological signs were observed in any of the groups. For further details see FIG. 14.

Conclusion: This study was designed to determine the efficacy of ABTL0812 either alone or combined with the SOC chemotherapy in the treatment of advanced pancreatic cancer. Gemcitabine in combination with Nab-Paclitaxel or Gemcitabine alone are the treatment of choice for most of advanced pancreatic cancer patients, thus we evaluated the potentiation of both treatments by their combination with ABTL081 2 and using suboptimal doses of chemotherapy, allowing for a reduction of the undesirable secondary effects. ABTL0812 potentiates both chemotherapy treatments while reducing toxicity, showing the highest tumor volume reduction compared with vehicle and with chemotherapy treatment alone. Additionally, ABTL081 2 administered alone shows similar efficacy to chemotherapy treatment and no clinicopathological or toxicity related signs in terms of total body weight were observed in any of the treatment groups.

2.9:
Efficacy Study of ABTL0812 in Neuroblastoma Xenograft Model (Cisplatin Sensitive) Alone or in Combination with Cisplatin
Study reference: ABTL081 2 notebook, pg 20-36
Study site: Laboratory of Translational Research in Pediatric Cancer at Vail d'Hebron Research Institute
GLP compliance: No
Test compound: ABTL081 2 (batch 002/20 13)
Reference compound: Cisplatin (Sigma #C22 10000)
Test System: Nu/nu female mice, SH-SY5Y cell line
Objective: To determine the efficacy of ABTL081 2 in the neuroblastoma cell line SH-SY5Y alone or in combination with cisplatin.

Methods: Immunodeficient athymic NMRI-Foxn1$^{nu}$/Foxn1$^{nu}$ nude mice were subcutaneously injected with SH-SY5Y cells. This cell line was genetically modified to express luciferase, which would allow the in vivo study not only of tumor size, but also of metastasis formation. When tumors reached an average volume of 80 mm$^3$, mice were randomly distributed into different treatment groups. ABTL081 2 was administered orally at 120 mg/kg daily. In parallel we used cisplatin, a drug included in the chemotherapy induction phase for the treatment of neuroblastoma. Cisplatin was administered at 2 mg/kg i.p. twice a week (Wang et al. 2010). Additionally, we studied the effect of combining ABTL081 2 with cisplatin at the indicated doses.

Results: A. Tumor size. This experiment revealed that ABTL081 2 inhibits tumor progression with an efficacy that is similar to cisplatin. After ten days of treatment, animals in the control group had to be sacrificed, due to ethical issues related to the size of the tumors. At this moment, half of the animals in the treated groups were sacrificed to measure tumor weight, hematological parameters and metastasis formation (see below). The choice of animals for sacrifice in these groups was performed according to statistical distribution of tumor size. Tumor weight measurement of the sacrificed mice confirmed the observation that ABTL081 2 efficacy is similar to the standard of care cisplatin. Analysis of tumor volume in the remaining animals in the treatment groups (approximately mice per group) revealed that the combination of ABTL081 2 with cisplatin results in a long-term stabilization of tumor growth. Monitoring of body weight indicated that treatment with ABTL081 2 transiently induces a minor loss of body weight (<10%). This effect is, however, recovered after some days. See FIG. 15 herein for further details.

B. Safety profile. Hematological analysis to evaluate safety of the treatments show that ABTL081 2 had no impact on blood hematocrit, however cisplatin induced anemia and reduced white blood cell count (see Table below). Cisplatin-associated anemia is a frequent side effect observed in patients treated with this chemotherapy drug (Wood and Hrushesky 1995).

regarding hematological parameters. Interestingly, the combination of ABTL081 2 with cisplatin results in stabilization of tumor progression for a longer period. Additionally, ABTL081 2 inhibited spontaneous metastasis formation in mouse models of neuroblastoma while cisplatin did not. These data further support that ABTL0812 could have enhanced therapeutic effects compared to current platinum-based chemotherapy treatments.

2.10:
Efficacy of ABTL0812 in Combination with Doxorubicin in a Human Triple Negative Breast Cancer (MDA-MB-231) Xenograft in Mice Study reference: Pending
Study site: Ability laboratory at UAB.
GLP compliance: No
Test compound: ABTL081 2 (batch 002/20 12)
Reference compounds: Doxorubicin (sigma #D1515)
Test System: Nu/nu male mice
Objective: Investigate the anti-tumor activity of ABTL081 2 alone and in combination with doxorubicin in a human triple negative breast cancer xenograft.

Methods: MDA-DB-231 cell line was routinely cultured in DMEM 10% FBS and cells in an exponential growth phase were harvested and counted for tumor inoculation. Mice were injected in one flank with 2.5×106 MDA-DB-23 1 cells suspended in 50 µl of growth medium without FBS and 50 µl of Matrigel (Corning #354234). Tumor volume was monitored 3 days a week and when tumors reached 100 mm$^3$ (between 50 and 150 mm$^3$), animals were homogeneously distributed into four treatment groups showing a similar average intragroup tumor volume, excluding tumors smaller than 50 mm$^3$ or greater than 150 mm$^3$ to minimize variabilities.

Treatment Groups were:
Vehicle group (n=7): treated orally with 200 µl of water+5% glycerol four days a week and two injections i.p. of 100 µl of saline solution once a week
ABTL081 2 (n=9): treated orally with 200 µl of 120 mg/kg of ABTL081 2 resuspended in water+5% glycerol 5 times a week

TABLE

Hematological analysis of animals in SH-SY5Y xenograft model. Blood was taken from animals at sacrifice and blood composition was determined with an automatic analyzer.

| Parameter | Vehicle | ABTL0812 | Cisplatin | ABTL0812 + Cisplatin |
|---|---|---|---|---|
| RBC ($\chi 10^6$/µL) | 7.9 ± 1.0 | 7.9 ± 0.4 | 6.8 ± 0.9* | 8.4 ± 1.1 |
| WBC ($\chi 10^3$/µL) | 3.8 ± 1.4 | 3.9 ± 1.3 | 3.0 ± 0.6 | 2.9 ± 1.5 |
| Hematocrit (%) | 41.5 ± 4.3 | 40.2 ± 1.4 | 37.3 ± 2.7 | 43.4 ± 5.3 |

*p < 0.05 by ANOVA followed by Bonferroni.

C. Metastasis formation. In order to investigate the effect of ABTL081 2 in metastasis formation we used a SH-SY5Y cell line transduced with a luciferase reporter vector. As described above, mice bearing xenograft tumors derived from this cell line were treated with ABTL081 2, cisplatin or the combination of both drugs. After ten days of treatment animals were sacrificed and metastasis were assessed ex vivo by monitoring luciferase-expressing cells in lung and liver. These analyses showed that ABTL081 2, either as a single agent or in combination with cisplatin, inhibited metastasis formation in these organs. Conversely, cisplatin alone had no significant effect in inhibiting metastasis formation compared to vehicle-treated animals.

Conclusion: ABTL081 2 as a single agent has an efficacy comparable to cisplatin, while having a better safety profile Doxorubicin (n=9): treated with 100 µl of 2 mg/kg of doxorubicin administered i.p. once a week
ABTL0812+doxorubicin (n=9): treated orally with 200 µl of 120 mg/kg of ABTL081 2 four days a week and 100 µl of 2 mg/kg of doxorubicin i.p. once a week Results: ABTL081 2 administered in combination with doxorubicin shows the best anti-tumor effect in vivo in xenografts derived from MDA-DB-231 cells. ABTL0812 administered alone showed a similar tumor volume reduction as doxorubicin alone, but the double combination ABTL0812 with doxorubicin shows the highest tumor volume reduction with significant difference at the end of the study. All treatment groups showed a similar evolution of total body weight, indicative of lack of toxicity associated to the treatments. For further details see FIG. 16 herein.

Conclusions: As described earlier, ABTL0812 reduces tumor growth in xenograft models of breast cancer derived from MDA-DB-231 cells. In this model, ABTL0812 potentiates the antitumor activity of doxorubicin. Doxorubicin therapy is a common treatment option for breast cancer patients, thus these results suggests that a combined therapy of ABTL0812 plus doxorubicin could have a clinical interest for the treatment of breast cancer patients.

2.11:
Efficacy of ABTL0812 in Combination with Gemcitabine and Cisplatin in a Human Cholangiocarcinoma (EGI-1) Xenograft in Mice
  Study reference: ABT-EI
  Study site: Liver Disease Group at Biodonostia Health Research Institute
  GLP compliance: No
  Test compound: ABTL0812 (batch 002/2012)
  Reference compounds: Gemcitabine-Hydrochloride (Sigma Aldrich G6423) and cisplatin (Sigma #C2210000)
  Test System: Nu/nu male mice
  Objective: Investigate the anti-tumor activity of ABTL0812 alone and in combination with gemcitabine and cisplatin in a human cholangiocarcinoma xenograft. Gemcitabine and cisplatin combo is one of one of the reference therapies for the treatment of cholangiocarcinoma.
  Methods: EGI-1 cell line was routinely cultured in DMEM 10% FBS and cells in an exponential growth phase were harvested and counted for tumor inoculation. Mice were injected in one flank with 1×106 H1957 cells suspended in 50 I of growth medium without FBS and 50 I of Matrigel (Corning #354234). Tumor volume was monitored 3 days a week and when tumors reached 100 mm$^3$ (between 50 and 150 mm$^3$), animals were homogeneously distributed into four treatment groups showing a similar average intragroup tumor volume, excluding tumors smaller than 50 mm$^3$ or greater than 150 mm$^3$ to minimize variabilities.
  Treatment groups were:
    Vehicle group (n=8): treated orally with 200 µl of water+5% glycerol four days a week and two injections i.p. of 100 µl of saline solution once a week
    ABTL0812 (n=8): treated orally with 200 µl of 120 mg/kg of ABTL0812 resuspended in water+5% glycerol 5 times a week
    Gemcitabine/cisplatin (n=8): treated with 100 µl of 50 mg/kg of gemcitabine administered i.p. and 100 µl of 2 mg/kg of cisplatin administered i.p. once a week
    ABTL0812+gemcitabine/cisplatin (n=8): treated orally with 200 µl of 120 mg/kg of ABTL0812 four days a week and 100 µl of 50 mg/kg of gemcitabine administered i.p. and 100 µl of 2 mg/kg of cisplatin administered i.p. once a week
  Results: ABTL0812 administered in combination with gemcitabine and cisplatin shows the best anti-tumor effect in vivo in xenografts derived from EGI-1 cells. Administration of gemcitabine and cisplatin reduced tumor volume compared with vehicle group, although without any statistically significant difference, in contrast to ABTL0812+gemcitabine and cisplatin treatment, that showed statistically significant tumor volume reduction compared to vehicle, ABTL0812 administered alone did not show tumor volume reduction compared to vehicle until the last day of treatment, where it showed a similar tumor volume as chemotherapy group. For further details see FIG. 17.
  Conclusions: As described earlier, ABTL0812 reduces tumor growth in xenograft models of cholangiocarcinoma derived from EGI-1 cells. In this model, ABTL0812 potentiates the antitumor activity of gemcitabine and cisplatin administration. gemcitabine and cisplatin therapy is a common treatment option for cholangiocarcinoma patients, thus these results suggests that a combined therapy of ABTL0812 plus gemcitabine and cisplatin could have a clinical interest for the treatment of cholangiocarcinoma patients.

Example 3: Toxicity of the Combination with Chemotherapy

Information about the toxicity of ABTL0812 combined with chemotherapeutic agents was obtained during the efficacy studies performed in immunosuppressed mice. A specific toxicology study of the combination of ABTL0812+/−paclitaxel+/−carboplatin has been performed.
  Study reference: N-02220
  Study site: Vivotecnia (Madrid, Spain)
  GLP Study: No
  Test compounds: ABTL0812 (batch 001R/2014), paclitaxel (Aurovitas, batch 68J5041), carboplatin (Sigma-Aldrich, batch LSBL7058v)
  Test system: CD-1 female mice, 12 weeks old.
  Objective: Determination of the toxicological profile of ABTL0812 in combination with carboplatin and paclitaxel after two-week administration.
  Methods: Forty-five female CD-1 mice were distributed by means of the body weight stratification method into nine experimental groups (A-I) (5 animals for group) that differed in the treatment or in the day on which the reference items (paclitaxel and carboplatin) were administered. The table below summarizes the treatment groups. Please note that the same administration schedule and doses were administered as in the previous efficacy studies.

TABLE

Groups of treatment to evaluate the toxicity of ABTL0812, paclitaxel, carboplatin and their combination in mice.

| Group | Treatment | Dose (mg/kg) | Schedule 1$^{st}$ period (day of the study) | 2$^{nd}$ period |
|---|---|---|---|---|
| A | Vehicle | — | 2-6 | 9-13 |
| B | ABTL0812 (p.o.) | 120 | 2-6 | 9-13 |
| C | Paclitaxel (i.p.) | 15 | 2 | 9 |
| D | Carboplatin (i.p.) | 50 | 2 | 9 |
| E | Paclitaxel (i.p.) | 15 | 2 | 9 |
|   | Carboplatin (i.p.) | 50 | 2 | 9 |
| F | ABTL0812 (p.o.) | 120 | 2-6 | 9-13 |
|   | Paclitaxel (i.p.) | 15 | 2 | 9 |
|   | Carboplatin (i.p.) | 50 | 2 | 9 |
| G | ABTL0812 (p.o.) | 120 | 2-6 | 9-13 |
|   | Paclitaxel (i.p.) | 15 | 1 | 8 |
|   | Carboplatin (i.p.) | 50 | 1 | 8 |
| H | ABTL0812 (p.o.) | 120 | 2-6 | 9-13 |
|   | Paclitaxel (i.p.) | 15 | 2 | 9 |
| I | ABTL0812 (p.o.) | 120 | 2-6 | 9-13 |
|   | Carboplatin (i.p.) | 50 | 2 | 9 |

The safety assessment relied on observed mortality, local and systemic clinical signs, body weight and food consumption recorded throughout the whole study. In addition, clinical pathology determinations (biochemistry and hematology) were performed before sacrifice in all animals. At the end of the observation period (one day after the last administration), all surviving animals were sacrificed and subjected to a gross necropsy. Moreover, the safety assessment was also based on the weight of selected target organs collected at sacrifice.

Results: The repeated oral treatment with test item and intraperitoneal treatment with reference items did not cause mortality. Neither local nor systemic clinical signs related with the treatment were recorded.

Slight differences in mean body weight gain were observed in animals over the course of the study. Most animals showed a tendency to decrease the body weight at the first four days of the study except for animals from group A (control group) and group C (treated with a dose of paclitaxel once weekly). However, in most animals no statistically significant differences were observed in the absolute body weight gain over the whole study period. Only animals from group F, which were administered with oral dose of ABTL0812 once daily for two 5-days periods and an intraperitoneal dose of paclitaxel and carboplatin once weekly (at the same day that the first oral dose of each period), had a markedly decrease in the body weight gain throughout the whole study period when compared to several animal groups (group A treated with vehicle, group C treated with paclitaxel and group E treated with a combination of paclitaxel and carboplatin).

Although it was not possible to perform statistical analysis due to small sample size, the estimated food consumption appeared to be higher in the animals from group A than in the rest of animals. Regarding clinical biochemistry parameters, lower creatinine and triglyceride levels were recorded in most groups when were compared with the control group. On the other hand, a statistically significant decrease was observed in hematocrit levels (for animals from group F) and platelets levels in groups treated with a combination of oral ABTL081 2 dose and intraperitoneal dose of paclitaxel and carboplatin (animals from groups F and G) when compared with control group. Although these values were within the normal range, an effect of the treatment in the clinical pathology parameters could not be ruled out.

The macroscopic observations at necropsy of all animals euthanized at the end of treatment did not reveal any relevant changes considered to be test item-related. The presence of white areas on the liver of animal ID32 and pigmentation on the pancreas of animals ID33 were observed. In addition, absolute and relative organ weights were similar among groups of treatment. The table below summarizes the most significant findings from a safety point of view.

Conclusion: Taking these results obtained into consideration, it can be concluded that under the assayed experimental conditions:

The repeated oral test item ABTL081 2 administration alone and in combination with a weekly intraperitoneal dose of Paclitaxel and Carboplatin did not cause mortality and was well tolerated, as neither local nor systemic clinical sings indicative of toxicity were observed in any of the animals over the course of the study.

Most animals kept the body weight throughout the study period. Only a statistically significant decrease was observed in animals treated with the combination of the test item and both reference items (at the same first day of each period).

The food consumption in animals from group A appeared to be higher than nearly all animals at the study period.

The clinical pathology (biochemical and hematological parameters) revealed differences statistically significant in treated groups when compared to control group. Despite most values were within the normal range for animals from this strain and sex, an effect of the treatment could not be ruled out. The effect on platelet count is due to carboplatin but an additional slight decrease in platelet count cannot be discarded when the three experimental drugs are combined.

No relevant effects of treatments on gross necropsy findings and absolute/relative organ weights were observed.

Example 4: ABTL0812 in Combination with Different Chemotherapeutic Agents-Human Data 4.1: A Phase I/II Open Label Study to Assess the Efficacy and Safety of ABTL0812 in Combination with Paclitaxel and Carboplatin in Patients with Advanced Endometrial Cancer or Squamous NSCLC.

A phase I/II clinical trial is being performed in patients with advanced endometrial cancer or squamous non-small cell lung carcinoma. This is a multi-center open-label trial in which ABTL081 2 is administered orally, starting at 1300 mg, three times daily in combination with chemotherapy.

TABLE

Most relevant biochemical and hematological findings in the toxicological study of ABTL081 2 and its combination with paclitaxel and carboplatin

| Group | Treatment (Day for PTX/CP) | Body Weight Gain (g) | | Biochemistry | | | Hematology | | |
|---|---|---|---|---|---|---|---|---|---|
| | | D 1-4 | D 8-11 | Urea mmol/L | Creat µmol/L | Triglyc mmol/L | WBC ×10$^3$/µL | RBC ×10$^6$/µL | PLT ×10$^3$/µL |
| A | Control | 0.784 | 0.630 | 8.10 | 14.35 | 2.31 | 6.96 | 9.24 | 1055 |
| B | ABTL | −0.804 | 0.138 | 3.66 | 9.18 | 0.94 | 5.94 | 9.57 | 1293 |
| C | PTX, D 2/9 | 0.354 | 0.442 | 9.50 | 9.74 | 1.31 | 6.28 | 9.59 | 1378 |
| D | CP, D 2/9 | −0.626 | −0.450 | 9.50 | 8.83 | 1.35 | 7.09 | 8.40 | 790 |
| E | PTX + CP, D 2/9 | −0.612 | 0.232 | 8.26 | 8.86 | 1.26 | 6.37 | 8.49 | 740 |
| F | ABTL + PTX + CP, D 2/9 | −1.322 | −0.540 | 6.82 | 9.07 | 1.00 | 4.53 | 8.41 | 470 |
| G | ABTL + PTC + CP, D 1/8 | −0.468 | −0.116 | 6.05 | 9.24 | 1.20 | 6.25 | 8.82 | 443 |
| H | ABTL + PTX, D 2/9 | −1.342 | 0.020 | 6.86 | 7.96 | 1.52 | 6.77 | 9.71 | 1249 |
| I | ABTL + CP, D 2/9 | −0.562 | −1.284 | 6.26 | 8.58 | 1.68 | 6.11 | 8.32 | 670 |

A. Objectives of the Trial

Phase I primary endpoint: To assess safety and tolerability of ABTL0812 plus paclitaxel+carboplatin in patients with advanced or metastatic endometrial cancer or squamous NSCLC at first line therapy Phase II primary endpoint: To evaluate the efficacy of ABTL0812 plus paclitaxel+carboplatin in patients with advanced or metastatic endometrial cancer or squamous NSCLC at first line therapy

B. Study Design

This study is not randomized, and all included patients are receiving ABTL0812 in addition to paclitaxel+carboplatin. This phase is divided in 2 periods:

Period 1: ABTL0812 is administered in combination with chemotherapy.

Period 2: After the finalization of the SOC cycles, ABTL0812 is taken as single therapy, up to 12 months from starting period 1.

CONCLUSION

Already obtained preliminary results from the human critical trial are positive—in the sense that these results indicate that there also in human is a synergistic effect in relation to use of the ABTL0812 compound in combination with paclitaxel and carboplatin in patients with advanced endometrial cancer or squamous cell cancer.

REFERENCES

1: EP2409963B1 (Lipopharma-filed in 2010)
2: Erazo, et al.; Clinical Cancer Research; 22 (10) May 15, 2016
3: News dated 22 Nov. 2016-published on the webpage of present applicant (AbilityPharma)
4: News dated Dec. 14, 2016-published on the webpage of present applicant (AbilityPharma)

The invention claimed is:

1. A pharmaceutical combination for the treatment of cancer comprising:
   (i) a Compound (A) which comprises a polyunsaturated fatty acid of formula COOH—CHOH—$(CH_2)_6$—(CH—CH—$CH_2)_2$—$(CH_2)_3$—$CH_3$ (ABTL0812), a pharmaceutically acceptable salt thereof, or a combination thereof
   and
   (ii) a Compound (B) which comprises at least one chemotherapeutic agent compound selected from the group consisting of a platinum-based agent, a nucleotide analog or precursor analog, an inhibitor of topoisomerase, or a combination thereof; and,
   wherein the cancer is a tumor.

2. The pharmaceutical combination of claim 1, wherein Compound (A) comprises a sodium salt of ABTL0812.

3. The pharmaceutical combination of claim 1, wherein the pharmaceutical combination is a single composition comprising both Compound (A) and Compound (B).

4. The pharmaceutical combination of claim 1, wherein the platinum-based agent is oxaliplatin.

5. The pharmaceutical combination of claim 1, wherein the nucleotide analog or precursor analog is fluorouracil.

6. The pharmaceutical combination of claim 1, wherein the inhibitor of topoisomerase is irinotecan.

7. The pharmaceutical combination of claim 1, wherein the platinum-based agent is oxaliplatin; the nucleotide analog or precursor analog is fluorouracil; and the inhibitor of topoisomerase is irinotecan.

8. A pharmaceutical combination for the treatment of a tumor comprising (i) ABTL0812, a pharmaceutically acceptable salt thereof, or a combination thereof, and, (ii) irinotecan.

9. A method to treat a tumor in a subject in need thereof comprising administering a therapeutically effective amount of a pharmaceutical combination of claim 8 to the subject.

10. A pharmaceutical combination for the treatment of a tumor comprising (i) ABTL0812, a pharmaceutically acceptable salt thereof, or a combination thereof; and, (ii) fluorouracil.

11. A method to treat a tumor in a subject in need thereof comprising administering a therapeutically effective amount of a pharmaceutical combination of claim 10 to the subject.

12. A method to treat a cancer in a subject in need thereof comprising administering a therapeutically effective amount of a pharmaceutical combination of claim 1 to the subject; wherein the cancer is a tumor.

13. The method of claim 12, wherein the tumor is selected from the group consisting of endometrial cancer, breast cancer, squamous cell cancer, lung cancer, endometrial cancer, cholangiocarcinoma, neuroblastoma, adenocarcinoma, pancreatic cancer, glioblastoma, and head and neck cancer.

14. The method of claim 12, wherein Compound (A) is administered orally.

15. The method of claim 12, wherein Compound (A) is administered as (i) a dose between 200 mg and 2,000 mg of Compound (A); or, (ii) a dose between 1,200 mg and 1,400 mg of Compound (A).

16. The method of claim 12, wherein Compound (A) is administered daily.

17. The method of claim 12, wherein Compound (B) is administrated intravenously.

18. The method of claim 17, wherein Compound (B) is administered intravenously via infusion solution or via infusion suspension.

19. The method of claim 12, wherein Compound (A) and Compound (B) are administered simultaneously, separately, or sequentially.

20. The method of claim 12, wherein the administration of a pharmaceutically effective amount of the pharmaceutical combination to the subject reduces tumor size, reduces tumor size progression, stabilizes tumor size, stabilizes tumor size progression, reduces metastasis formation, increases survival rate, or a combination thereof.

* * * * *